(12) United States Patent
Genovese et al.

(10) Patent No.: US 12,336,907 B2
(45) Date of Patent: Jun. 24, 2025

(54) TIP ASSEMBLIES, SYSTEMS, AND METHODS FOR FRACTURING A FRAME OF A DEPLOYED PROSTHESIS

(71) Applicant: Medtronic Vascular, Inc., Santa Rosa, CA (US)

(72) Inventors: Matthew Genovese, Windsor, CA (US); Christopher Storment, Sonoma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 280 days.

(21) Appl. No.: 18/056,429

(22) Filed: Nov. 17, 2022

(65) Prior Publication Data
US 2023/0079043 A1 Mar. 16, 2023

Related U.S. Application Data

(62) Division of application No. 16/401,235, filed on May 2, 2019, now Pat. No. 11,540,917.
(Continued)

(51) Int. Cl.
*A61F 2/24* (2006.01)
*A61B 17/32* (2006.01)
(Continued)

(52) U.S. Cl.
CPC .......... *A61F 2/2427* (2013.01); *A61F 2/2418* (2013.01); *B26D 7/086* (2013.01);
(Continued)

(58) Field of Classification Search
CPC ...... A61F 2/2418; A61F 2/2427; A61F 2/243; A61F 2/011; A61F 2/95; A61F 2002/9528; A61F 2002/9534; A61F 2250/001; A61F 2250/0082; A61B 17/50; A61B 17/320068; A61B 17/22012; A61B 2017/00623;
(Continued)

(56) References Cited

U.S. PATENT DOCUMENTS

| 4,823,793 A | 4/1989 | Angulo et al. |
| 5,087,264 A | 2/1992 | Miller et al. |

(Continued)

OTHER PUBLICATIONS

Communication pursuant to Article 94(3) EPC issued in EP Application No. 19 724 042.7, dated Jun. 19, 2023.
(Continued)

*Primary Examiner* — Diane D Yabut

(57) ABSTRACT

A system for fracturing a frame of a deployed prosthesis with ultrasonic vibration includes a shaft, a tip assembly, an ultrasonic electric generator, and an ultrasonic transducer. The shaft includes a proximal portion and a distal portion. The tip assembly is coupled to the distal portion of the shaft. The tip assembly includes a cutting edge. The ultrasonic transducer is electrically coupled to the ultrasonic generator. Ultrasonic vibration generated by the ultrasonic transducer is translated to the tip assembly. The cutting edge of the tip assembly is configured to focus the vibration of the tip assembly onto a frame of a deployed prosthesis to fracture the frame of the prosthesis. The ultrasonic transducer may be coupled to the proximal portion or the distal portion of the shaft.

16 Claims, 35 Drawing Sheets

Related U.S. Application Data

(60) Provisional application No. 62/666,480, filed on May 3, 2018.

(51) Int. Cl.
  *A61F 2/95* (2013.01)
  *B26D 7/08* (2006.01)

(52) U.S. Cl.
  CPC .......... *A61B 2017/320072* (2013.01); *A61B 2017/320075* (2017.08); *A61F 2002/9534* (2013.01); *A61F 2250/001* (2013.01); *A61F 2250/0063* (2013.01); *A61F 2250/0093* (2013.01)

(58) Field of Classification Search
  CPC ......... A61B 2017/2944; A61B 2017/320072; A61B 2017/320074; A61B 2017/320075; A61B 2017/320077; B26D 7/086
  See application file for complete search history.

(56) References Cited

U.S. PATENT DOCUMENTS

| | | | |
|---|---|---|---|
| 5,354,309 A * | 10/1994 | Schnepp-Pesch | A61F 2/92 606/198 |
| 5,397,333 A | 3/1995 | Knoepfler | |
| 6,036,667 A | 3/2000 | Manna et al. | |
| 8,961,593 B2 | 2/2015 | Bonhoeffer et al. | |
| 9,504,566 B2 | 11/2016 | Guttenberg et al. | |
| 9,592,079 B1 * | 3/2017 | Pursley | A61B 17/50 |
| 9,636,219 B2 | 5/2017 | Keidar et al. | |
| 9,717,513 B2 | 8/2017 | Golan | |
| 2002/0198555 A1 * | 12/2002 | White | A61B 17/320092 606/169 |
| 2006/0074484 A1 | 4/2006 | Huber | |
| 2008/0009848 A1 | 1/2008 | Paraschiv et al. | |
| 2010/0280597 A1 * | 11/2010 | Hoerstrup | A61F 2/2418 623/1.26 |
| 2012/0010699 A1 | 1/2012 | Vesely | |
| 2013/0245746 A1 | 9/2013 | Trollsas et al. | |
| 2016/0228181 A1 | 8/2016 | Berguer et al. | |
| 2016/0242889 A1 | 8/2016 | Brown | |
| 2016/0296331 A1 | 10/2016 | Chung et al. | |
| 2016/0361084 A1 | 12/2016 | Weisenburgh et al. | |
| 2017/0000603 A1 | 1/2017 | Conklin et al. | |
| 2017/0000604 A1 | 1/2017 | Conklin et al. | |
| 2017/0000636 A1 | 1/2017 | Donatelli et al. | |
| 2017/0042528 A1 | 2/2017 | Ellegala | |
| 2017/0071732 A1 | 3/2017 | Conklin et al. | |
| 2018/0042634 A1 | 2/2018 | Conlon et al. | |
| 2018/0042635 A1 | 2/2018 | Roeder et al. | |
| 2019/0059985 A1 | 2/2019 | Shelton et al. | |

OTHER PUBLICATIONS

International Search Report and Written Opinion of the International, issued in International Application No. PCT/US2019/030439, dated Jul. 15, 2019.

* cited by examiner

TIP ASSEMBLIES, SYSTEMS, AND METHODS FOR FRACTURING A FRAME OF A DEPLOYED PROSTHESIS

CROSS-REFERENCE TO RELATED APPLICATIONS

This application is a divisional of U.S. patent application Ser. No. 16/401,235, filed May 2, 2019, which claims priority under 35 U.S.C. § 119(e) of U.S. Provisional Application No. 62/666,480, filed May 3, 2018, the contents of both which are incorporated by reference herein in their entirety.

FIELD OF THE INVENTION

The present invention relates to systems and methods for fracturing a frame of a deployed stented prosthesis. More particularly, the present invention relates to a system with a tip assembly for fracturing a frame of a deployed stented heart valve prosthesis with ultrasonic energy.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To ensure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Stented heart valve prostheses have been developed for repair and replacement of diseased and/or damaged heart valves, and heart valve replacement has become a routine surgical procedure for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter delivery and implantation of replacement cardiac valves to solve the problems presented by traditional open surgery and minimally invasive surgical methods. In such methods, a stented heart valve prosthesis, also known generally as a valve prosthesis, is compacted for delivery in a catheter and then advanced, for example through an opening in the femoral artery, through the inferior vena cava, through the interatrial septum, where the valve prosthesis is then deployed in the annulus of the native heart valve.

Various types and configurations of valve prostheses are available for percutaneous valve replacement procedures. In general, stented heart valve prostheses designs attempt to replicate the function of the heart valve being replaced and thus will include valve leaflet-like structures. Valve prostheses are generally formed by attaching a bioprosthetic valve to a frame made of a wire or a network of wires. Such a valve prosthesis can be collapsed radially to introduce the valve prosthesis into the body of the patient percutaneously through a catheter. The valve prosthesis may be deployed by radially expanding it once positioned at the desired deployment site.

A deployed valve prosthesis in a patient may need to be replaced for reasons including the valve prosthesis reaching its useful service life, restenosis and/or calcification of the deployed valve prosthesis, or physical growth of the patient such that the deployed valve prosthesis is no longer sufficient. A deployed valve prosthesis may be percutaneously replaced with a new valve prosthesis in what is referred to as a valve-in-valve replacement procedure, wherein the new valve prosthesis is deployed within the older, previously deployed valve prosthesis. However, expanding the deployed valve prosthesis with a balloon or a new valve prosthesis within a deployed stenotic and/or calcified valve prosthesis may not result in a large enough orifice or effective diameter to accommodate the new valve prosthesis. More specifically, the balloon or new self-expanding valve prosthesis may not have sufficient outward radial force to expand the old, deployed stenotic and/or calcified valve prosthesis enough to provide sufficient blood flow through the newly deployed valve prosthesis. Accordingly, there is a need for equipment and methods to safely expand a deployed valve prosthesis prior to valve-in-valve replacement.

BRIEF SUMMARY OF THE INVENTION

Embodiments hereof further relate to a system for fracturing a frame of a deployed prosthesis, e.g., a valve prosthesis. The system includes a shaft, a tip assembly, an ultrasonic electric generator, and an ultrasonic transducer. The shaft includes a proximal and a distal portion. The tip assembly is coupled to the distal portion of the shaft and includes a cutting edge. The ultrasonic transducer is electrically coupled to the ultrasonic electric generator. Ultrasonic vibration generated by the ultrasonic transducer is translated to the tip assembly. The cutting edge of the tip assembly is configured to focus the ultrasonic vibration onto a frame of a deployed valve prosthesis to fracture the frame.

Embodiments hereof further relate to a tip assembly for fracturing a frame of a valve prosthesis with ultrasonic vibration. The tip assembly includes at least one segment and a cutting edge coupled to the at least one segment. The cutting edge is configured to focus ultrasonic vibration of the tip assembly.

Embodiments hereof also relate to a method of fracturing a frame of a deployed valve prosthesis. The system is advanced to the site of a deployed valve prosthesis. The system includes a shaft, a tip assembly, an ultrasonic electric generator, and an ultrasonic transducer. The tip assembly of the system is positioned at a connection point to be fractured of a frame of the deployed valve prosthesis. A cutting edge of the tip assembly is placed in contact with the desired connection point to be fractured. A longitudinal force, either in a distal or a proximal direction, is applied to the shaft to hold the cutting edge of the tip assembly in contact with the desired connection point. The ultrasonic generator and the ultrasonic transducer are activated. When the connection point of the frame has fractured, the ultrasonic generator and the ultrasonic transducer are deactivated.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a shaft or system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a device to be implanted into a vessel, such as a heart valve prosthesis, are used with reference to the direction of blood flow from the heart. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of a system for fracturing a frame of a deployed heart valve prosthesis, the invention may also be used for fracturing a frame of a non-valve prosthesis, for example, in other body passageways where it is deemed useful. Furthermore, there is no intention to be bound by any expressed or implied theory presented in the preceding technical field, background, brief summary or the following detailed description.

Figure 1:
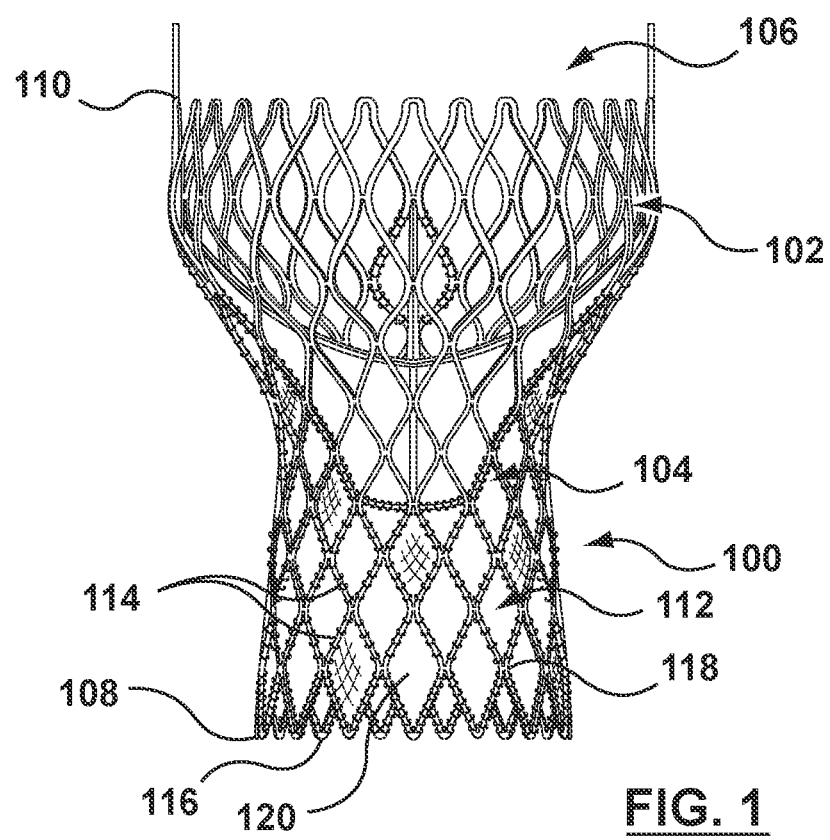
FIG. 1 depicts a schematic illustration of an exemplary valve prosthesis for use with embodiments hereof.
Figure 2:
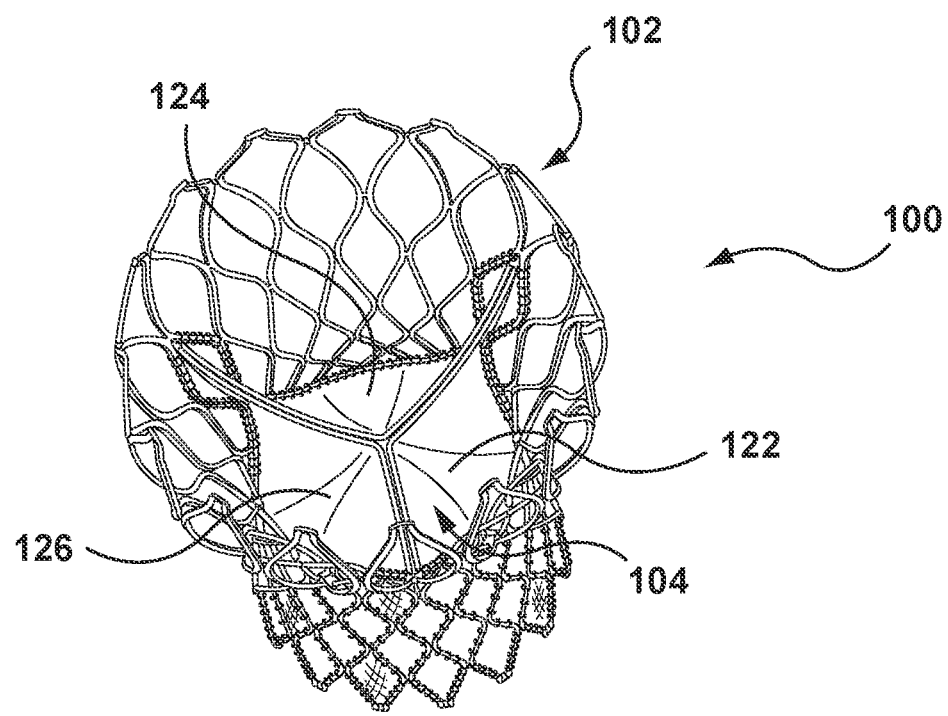
FIG. 2 depicts a perspective illustration of the valve prosthesis of FIG. 1.

The present invention in various embodiments relates to a system with a tip assembly for fracturing or breaking a portion of a frame of a deployed valve prosthesis at a site of a native valve utilizing ultrasonic vibration. "Fracturing", "fractured", or "fracture" as used herein is meant to convey that a structure is separated, broken, divided, or moved apart or caused to be separated, broken, divided or moved apart. The frame to be fractured may be a frame or stent of a heart valve prosthesis 100, hereafter referred to as the valve prosthesis 100 for sake of brevity, as shown in the embodiment of FIGS. 1 and 2. The valve prosthesis 100 includes a frame 102 supporting a prosthetic valve 104. For example, the valve prosthesis 100 useful with the present disclosure can be a prosthesis sold under the trade name Evolut R® available from Medtronic CoreValve, LLC and as described in U.S. Pat. No. 8,226,710 to Nguyen et al., which is incorporated by reference herein in its entirety. The valve prosthesis 100 has a radially expanded configuration when deployed. The valve prosthesis 100 is illustrated herein in order to facilitate description of systems and tip assemblies for fracturing a deployed frame of a valve prosthesis with ultrasonic vibration prior to a procedure such as a valve-in-valve replacement, as described below according to embodiments hereof. While the valve prosthesis 100 illustrated herein is of a specific construction and structure, it is not meant to be limiting, and alternate valve prostheses can be used with the methods and devices described herein. The valve prosthesis 100 is merely exemplary. It is understood that any number of alternate valve prostheses can be used with the methods and devices described herein. Further, while the valve prosthesis 100 is described herein for used as an aortic valve prosthesis, this is only exemplary, and the valve prosthesis may assume various configurations for use at other locations within the heart and the body.

The frame 102, as shown in FIG. 1, also referred to as a stent or support structure, can have, for example, a flared, funnel-like or hyperboloid shape. Accordingly, the frame 102 defines a lumen 106 extending from an inflow or proximal end 108 to an outflow or distal end 110. The frame 102 includes a radially collapsed configuration for delivery and a radially expanded configuration when deployed. The frame 102 is a structural component of the valve prosthesis 100, and thus, when the frame 102 is in the radially expanded configuration, the valve prosthesis 100 is in the radially expanded configuration. The frame 102 is configured to engage tissue at the annulus of the native heart valve when the frame is in the radially expanded configuration. The frame 102 is further configured to provide a secure mounting surface for the prosthetic valve 104. The frame 102 includes a plurality of cells 112 formed by a plurality of struts 114 joined by bent segments or crowns 116. The cells 112 may have sizes that vary along the length of the stent-like frame 102. In the embodiment shown in FIG. 1, selected longitudinally adjacent crowns 116 may be joined by, for example, at a connection point 118. However, the invention is not limited to the pattern shown in FIG. 1. When configured as a replacement for an aortic valve, the inflow end 108 extends into and anchors within the aortic annulus of a patient's left ventricle and the outflow end 110 is positioned in the patient's ascending aorta. Embodiments of the frame 102 may include structural components such as, but not limited to the plurality of struts 114 arranged relative to each other to provide a desired compressibility and strength. As described herein, the frame 102 is self-expanding from the radially collapsed configuration to the radially expanded configuration. Alternatively, the frame 102 may be balloon expandable or mechanically expandable. The frame 102 may be made from materials such, but not limited to nickel-titanium alloys (e.g., NITINOL) and other super-elastic materials. "Self-expanding" as used herein means that a structure has a mechanical memory to return to the radially expanded configuration. Mechanical memory may be imparted on the structure that forms the stent-like frame 102 using techniques understood in the art.

As previously described herein, the valve prosthesis 100 includes the prosthetic valve 104 within the interior of the frame 102. The prosthetic valve 104 may further include a skirt 120 affixed to the frame 102. The prosthetic valve 104 is configured as a one-way valve to allow blood flow in one direction and thereby regulate blood flow there through. The prosthetic valve 104 is capable of blocking flow in one direction to regulate flow via valve leaflets. More particularly, when the valve prosthesis 100 is configured for placement within a native heart valve having three (3) leaflets such as the aortic valve, as shown in FIGS. 1 and 2, the prosthetic valve 104 may include three (3) valve leaflets 122, 124, 126 to form a tricuspid replacement valve that closes with pressure on the outflow and opens with pressure on the inflow. In other embodiments in accordance herewith, the prosthetic valve 104 may be a bicuspid replacement valve or may be a single leaflet replacement valve. The valve leaflets are sutured or otherwise securely and sealingly attached to an inner circumference of the frame 102.

The valve leaflets 122, 124, 126 of the prosthetic valve 104 may be made of natural pericardial material obtained from, for example, heart valves, aortic roots, aortic walls, aortic leaflets, pericardial tissue, bypass grafts, blood vessels, intestinal submucosal tissue, umbilical tissue and the like from humans or animals, such as tissue from bovine, equine or porcine origins. Alternatively, the valve leaflets of the prosthetic valve 104 may be made of synthetic materials suitable for use as heart valve prosthesis leaflets in embodiments hereof including, but are not limited to polyester, polyurethane, cloth materials, nylon blends, and polymeric materials.

Figure 3:
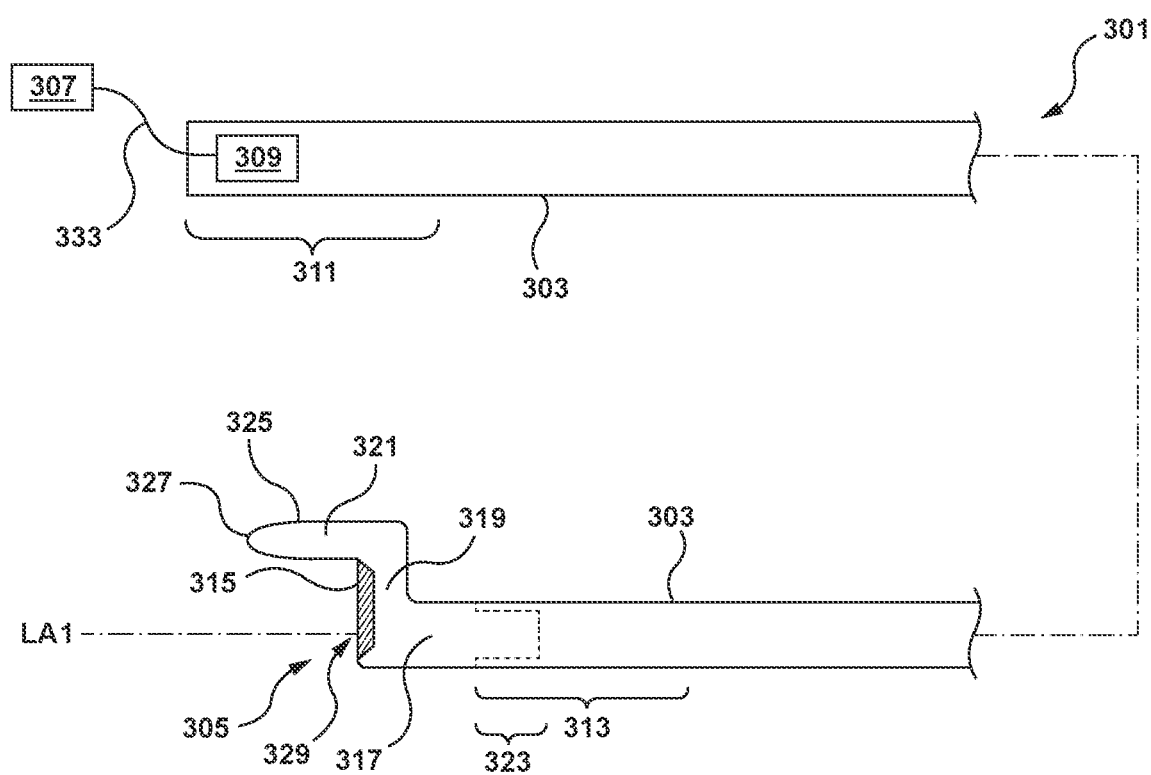
FIG. 3 depicts a side view illustration of a system according to an embodiment hereof, wherein the system includes an ultrasonic transducer at a proximal portion of a shaft of the system and a tip according to an embodiment hereof.
Figure 4:
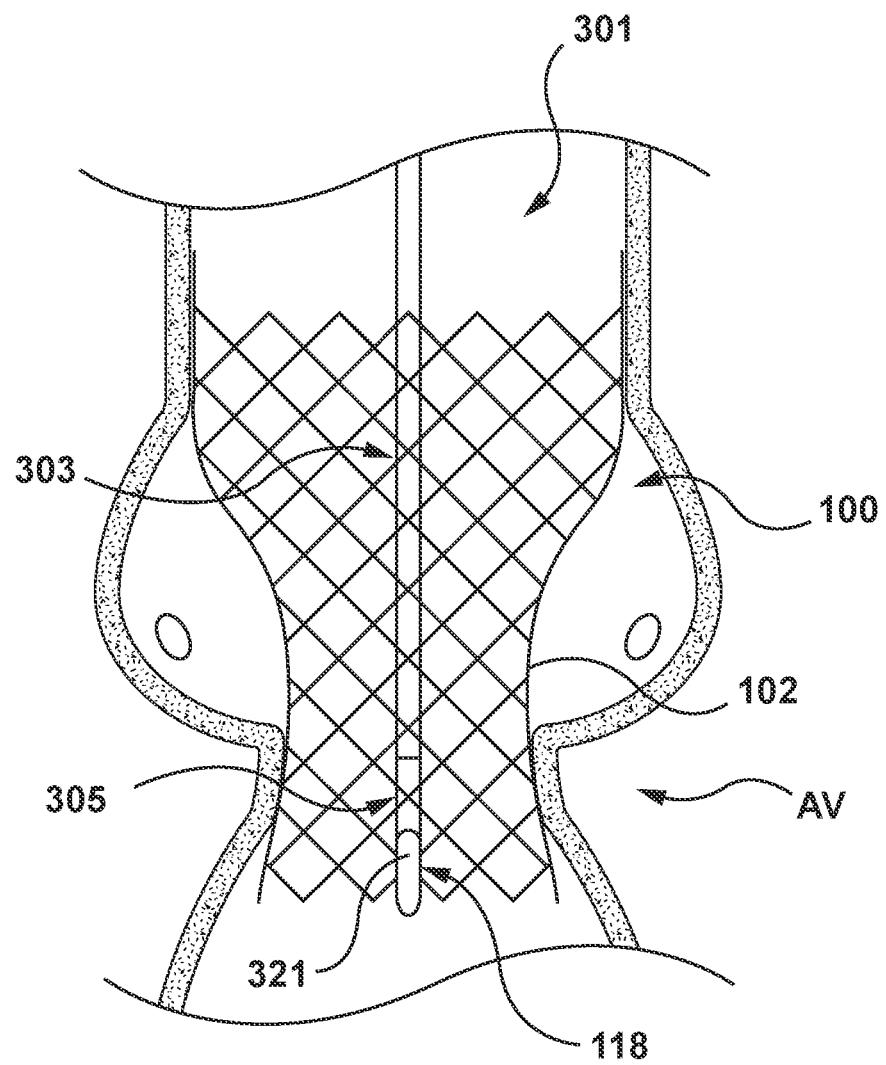
FIG. 4 depicts a sectional cut-away illustration of a heart and the system of FIG. 3 positioned at a desired connection point to be fractured of a frame of a deployed valve prosthesis.

A system 301 for fracturing a frame of a deployed valve prosthesis, such as the frame 102 of the valve prosthesis 100 previously described herein, with ultrasonic vibration according to an embodiment hereof is shown in FIGS. 3-5. The system 301 includes a shaft 303, a tip assembly 305, an ultrasonic electric generator 307, and an ultrasonic transducer 309. The system 301 is configured to fracture at least one desired connection point 118 of the deployed valve prosthesis 100 with ultrasonic vibration. For example, ultrasonic fracturing of the frame 102 may be required prior to the deployment of a new replacement valve prosthesis in a valve-in-valve replacement procedure. In another example, ultrasonic fracturing of the frame 102 may be required to expose access to a coronary sinus for a coronary procedure. More specifically, the system 301 is configured to safely fracture the frame 102 of the deployed valve prosthesis 100 without damaging the surrounding tissue.

The shaft 303 is a flexible shaft with a generally tubular shape and includes a proximal portion 311 and a distal portion 313. "Generally" as used herein, particularly with respect to the terms "tubular", "circular", and "traverse" means within normal manufacturing tolerances. In the embodiment of FIGS. 3-5, the ultrasonic transducer 309 is coupled to the proximal portion 311 and the tip assembly 305 is coupled to the distal portion 313 as described below. The shaft 303 is configured to translate vibration or movement from the proximal portion 311 to the distal portion 313. More specifically, the shaft 303 is configured to translate ultrasonic vibration generated by the ultrasonic transducer 309 to the tip assembly 305. "Translated" as used herein means that an ultrasonic vibration is transferred, conveyed, transmitted or otherwise passed from one component, for example the shaft 303 to another component, for example the tip assembly 305. Although the shaft 303 is described herein as a single component, this is not meant to limit the design, and the shaft 303 may include components such as, but not limited to a proximal shaft, a distal shaft, a handle, or other components suitable for the purposes described herein. The shaft 303 may be constructed of materials such as, but not limited to stainless steel, titanium, tantalum, tungsten, or other materials suitable for the purposes of the present disclosure.

The shaft 303 is configured to be disposed with a portion of the shaft 303 extending outside of a patient, i.e., the proximal portion 311, and a portion of the shaft 303 positioned in situ within a body lumen or vessel, i.e., the distal portion 313. The shaft 303 is further configured to deliver and position the tip assembly 305 of the system 301 at the site of the deployed valve prosthesis 100, as described below. Accordingly, the shaft 303 and the tip assembly 305 are each sized and configured to be advanced through a vasculature in a minimally invasive manner.

The tip assembly 305 according to an embodiment hereof for fracturing a frame of a deployed valve prosthesis, such as the valve prosthesis 100 previously described, is shown in FIGS. 3-5A. The tip assembly 305 includes a sharpened edge 315, a first segment 317, a second segment 319, and a third segment 321. A proximal portion 323 of the tip assembly 305 is coupled to the distal portion 313 of the shaft 303. The tip assembly 305 is configured to translate ultrasonic vibration of the tip assembly 305 onto the frame 102 of the deployed valve prosthesis 100 to fracture the frame 102 of the deployed valve prosthesis 100, as described below. In the embodiment of FIGS. 3-5A, each of the segments 317, 319, and 321 of the tip assembly 305 includes a generally tubular shape with a generally circular cross-section. The tip assembly 305 may be constructed of materials such as, but not limited to stainless steel or other materials suitable for the purposes of the present disclosure. The tip assembly 305 may be coupled to the shaft 303, for example, and not by way of limitation by adhesives, welding, clamping, or other coupling methods as appropriate. While the tip assembly 305 is shown coupled to the shaft 303 in a particular coupling configuration, this is by way of example and not limitation, and it will be understood that other coupling configurations may be utilized. For example, and not by way of limitation, a proximal end of the tip assembly 305 may be coupled to a distal end of the shaft 303. Further, while the first, second, and third segments 317, 319, and 321 of the tip assembly 305 have each been described with a generally tubular shape and a generally circular cross-section, this is by way of example and not limitation. The first, second, and third segments 317, 319, and 321 may each have alternative shapes including, but not limited to shapes with an oblong cross-section, a rectangular cross-section, or any other suitable shape.

As best shown in FIG. 3, the first segment 317 includes a first longitudinal axis LA1. The second segment 319 of the tip assembly 305 extends radially outward from, or generally transverse to the first segment 317. The third segment 321 extends distally from the second segment 319 such that the third segment 321 is generally parallel to and radially outward from the first longitudinal axis LA1. Stated another way, the third segment 321 is generally parallel to and radially spaced apart from the first segment 317 and the first longitudinal axis LA1. In the embodiment of FIGS. 3-5A, the third segment 321 includes a conical portion 325 and a rounded or atraumatic tip 327 at a distal portion thereof. The third segment 321 is configured such that the third segment 321 will not damage tissue during delivery of the tip assembly 305 to the deployed valve prosthesis 100 or during fracturing of the frame 102, as described below. While the tip assembly 305, and more precisely the first segment 317, the second segment 319, and the third segment 321 have been described herein as a single component, this is not meant to limit the design and the first segment 317, the second segment 319, and the third segment 321 may be separate components coupled together by methods such as but not limited adhesives, welding, or other coupling methods as appropriate. Although the first segment 317, the second segment 319, and the third segment 321 are each described in FIGS. 3-5 with a generally circular cross-section, this is by way of example and not limitation. It will be understood that other cross-sectional shapes may be utilized for each segment of the tip assembly 305 including, but not limited to an elliptical shape. Moreover, while the embodiment of FIGS. 3-5A show the third segment 321 with a conical portion 325, this too is by way of example and not limitation and other shapes of the third segment 321 may be utilized including a cylindrical shape, or any other shape suitable for the purposes described herein.

In the embodiment of FIGS. 3-5A, the sharpened edge 315 is disposed on a distal facing surface 329 of the tip assembly 305. The sharpened edge 315 is configured to focus or concentrate ultrasonic vibration or motion of the tip assembly 305 along the first longitudinal axis LA1 onto the desired connection point 118 of the frame 102 of the deployed valve prosthesis 100 to fracture the frame 102 at the desired connection point 118, as described below. The sharpened edge 315 may be formed by methods such as, but not limited to laser ablation, mechanical sharpening, chemical etching, or any other method suitable for the purposes described herein.

Tip assembly 305, as well as other embodiments of tip assemblies described herein, include the sharpened edge 315 configured to focus or concentrate ultrasonic vibration or motion onto a desired connection point of the frame of the deployed valve prosthesis to fracture the frame at the desired connection point. However, a blunt or flat edge may be utilized rather than a sharpened edge. The ultrasonic vibration or motion is less focused or targeted onto a desired connection point of the frame of the deployed valve prosthesis with a blunt or flat edge, but the blunt or flat edge poses less of a risk of injury to the surrounding anatomy during treatment. As such, as used herein, a "cutting edge" is intended to cover both sharpened edges described herein as well as blunt edges that are suitable for fracturing the frame of a deployed valve prosthesis at a desired connection point.

In the embodiment of FIGS. 3-5A, the ultrasonic electric generator 307 is disposed external of the shaft 303 and the ultrasonic transducer 309 is disposed at and coupled to the proximal portion 311 of the shaft 303. The ultrasonic electric generator 307 is electrically coupled to the ultrasonic transducer 309 by a connection 333. The connection 333 may be any electrical connection capable of carrying an ultrasonic electric signal generated by the ultrasonic electric generator 307 to the ultrasonic transducer 309. The ultrasonic electrical generator 307 creates an electrical signal that is, for example, greater than or equal to 20 kHz. The electric signal is transmitted through the connection 333 to the ultrasonic transducer 309, which converts the electrical signal to physical motion in the form of ultrasonic mechanical vibration. The ultrasonic vibration is then translated to the coupled proximal portion 311 of the shaft 303. More precisely, the ultrasonic vibration generated by the ultrasonic transducer 309 is translated to the tip assembly 305. The power and frequency of the ultrasonic vibration may be selected based upon the application requirements of the procedure to be performed. In a non-limiting example, the ultrasonic electric generator 307 and the ultrasonic transducer 309 may each have a frequency of 20 kHz, a power rating of 50 watts, and longitudinally move the coupled shaft 303 and the tip assembly 305 between 5 and 10 microns along the first longitudinal axis LA1. The ultrasonic transducer 309 may be coupled to the shaft 303 for example, and not by way of limitation by adhesives, welding, clamping, or other coupling methods as appropriate. While the ultrasonic electric generator 307 is shown disposed external of the shaft 303, this is by way of example and not limitation, and the ultrasonic electric generator 307 may be disposed at other locations of the system 301 such as, but not limited to the shaft 303, or any other suitable location. Further, while the ultrasonic transducer 309 is shown disposed at a specific location within the shaft 303, this too is by way of example and not limitation. It will be understood that the ultrasonic transducer 309 may be disposed at a variety of locations, including, but not limited to a location within the shaft 303, on an outer surface of the shaft 303, at the proximal portion 311 of the shaft 303, at the distal portion 313 of the shaft 303, or at any other suitable location.

With reference to FIGS. 3-5C, the interaction of the various components of the system 301 will now be described to fracture a connection point, such as the connection point 118 of the frame 102 of the deployed valve prosthesis 100, as shown in FIGS. 4 and 5A-5C. With the components of the system 301 assembled and configured as described above, the system 301 is advanced to the site of the deployed valve prosthesis 100, which in the example of FIGS. 4 and 5A-5C is deployed within a native aortic valve AV. The third segment 321 of the tip assembly 305 is brought into apposition with the desired connection point 118 to be fractured.

The tip assembly 305 is manipulated to position the sharpened edge 315 (obscured from view in FIG. 4 but visible in FIG. 5A) of the tip assembly 305 in contact with the connection point 118 to be fractured. In the embodiment of FIGS. 3-5A, this includes manipulating the tip assembly 305 radially outward such that the third segment 321 passes through one cell 112 of the frame 102 that is adjacent to an outflow facing surface 128 of the desired connection point 118 to be fractured. The atraumatic tip 327 of the third segment 321 prevents damage to the adjacent tissue as the third segment 321 is manipulated radially outward and the sharpened edge 315 is placed adjacent the desired connection point 118.

Figure 5A:
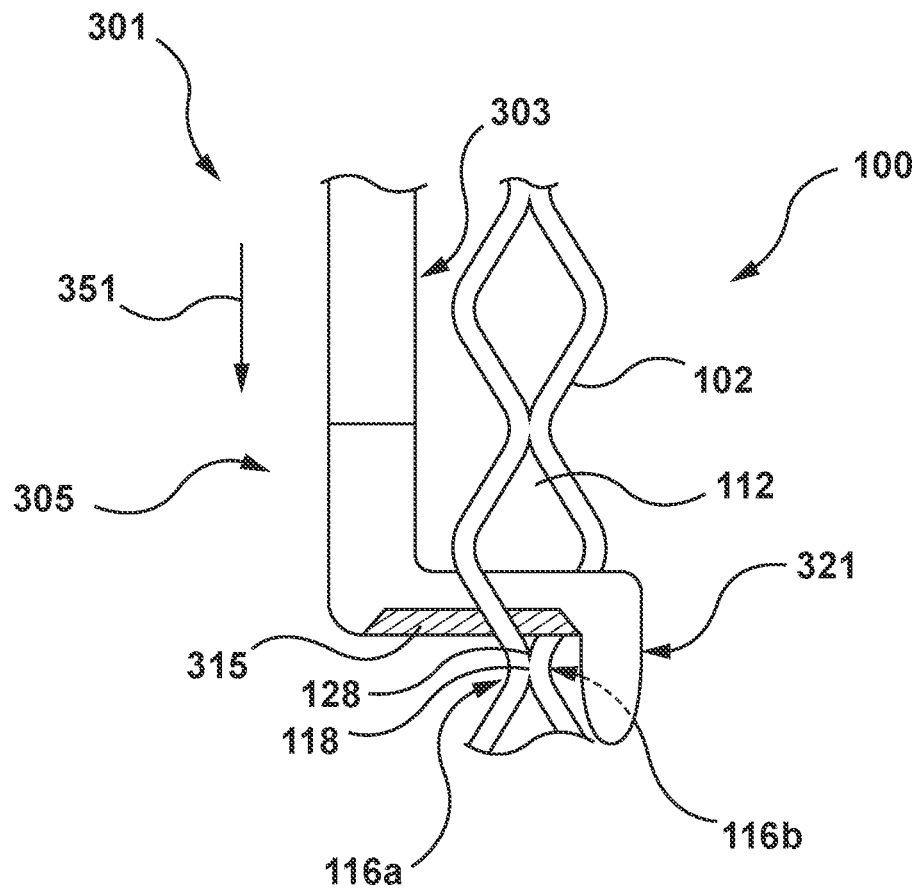
FIG. 5A depicts a close-up perspective illustration of a tip assembly of the system of FIG. 4, wherein the tip assembly is adjacent to and in contact with the desired connection point of the frame of the deployed valve prosthesis.

When the sharpened edge 315 is positioned adjacent to the outflow facing surface 128 of the desired connection point 118 to be fractured as described above, the system 301 is distally advanced to place the sharpened edge 315 in contact with the outflow facing surface 128 of the connection point 118 to be fractured, as best shown in FIG. 5A. It will be understood that only a portion of the frame 102 is illustrated in FIG. 5A, and that the omitted portions of the frame 102 have been omitted for clarity.

A constant force in the distal direction, indicated in FIG. 5A by an arrow 351, is maintained on the shaft 303 to keep the sharpened edge 315 in contact with the desired connection point 118. The distal force (arrow 351) is seen as a compressive force on the shaft 303.

Figure 5B:
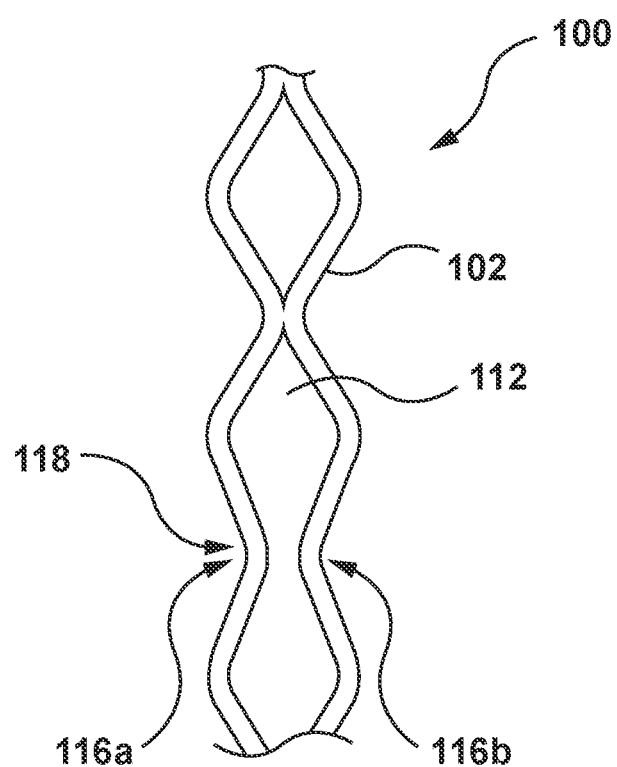
FIG. 5B depicts a close-up perspective illustration of the valve prosthesis of FIG. 5A, wherein the connection point has been fractured and the tip assembly of the system has been omitted for clarity.

When the force in the distal direction (indicated by the arrow 351) is holding the sharpened edge 315 in contact with the desired connection point 118, the ultrasonic electric generator 307 and the ultrasonic transducer are activated. The ultrasonic vibration of the ultrasonic transducer 309 is translated to the coupled proximal portion 311 of the shaft 303. The shaft 303 translates the ultrasonic vibration to the distal portion 313 of the shaft 303, and to the tip assembly 305 coupled thereto. The sharpened edge 315 of the tip assembly 305 focuses the mechanical vibration onto the contacted desired connection point 118. The ultrasonic vibration of the sharpened edge 315 against the connection point 118, combined with the constant force in the distal direction (indicated by the arrow 351) holding the sharpened edge 315 against the connection point 118, fractures or breaks the desired connection point 118. Fracturing of the connection point 118 separates the adjacent crowns 116a and 116b of the valve prosthesis 100 at the fractured connection point 118 such that the adjacent crowns 116a and 116b are no longer in contact with each other, as shown in FIG. 5B, which shows the fractured connection point 118 with the tip assembly 305 of the system 301 omitted for clarity. By focusing the ultrasonic vibration onto a known point, i.e. the desired connection point 118, the sharpened edge 315 breaks or fractures the frame 102 at a known location and in a known and predictable manner that provides a level of embolic protection by reducing or eliminating the creation of shards during the fracturing process. Additionally, fracturing the connection point 118 with the sharpened edge 315 yields an anatomically safe fracture point that reduces the danger of damage to the surrounding tissue.

When the desired connection point 118 has been fractured, the ultrasonic electric generator 307 and the ultrasonic transducer are deactivated. If another connection point 118 is to be fractured, the process of maneuvering the tip assembly 305 to the next desired connection point 118 and fracturing of said next desired connection point 118 is repeated.

Figure 5C:
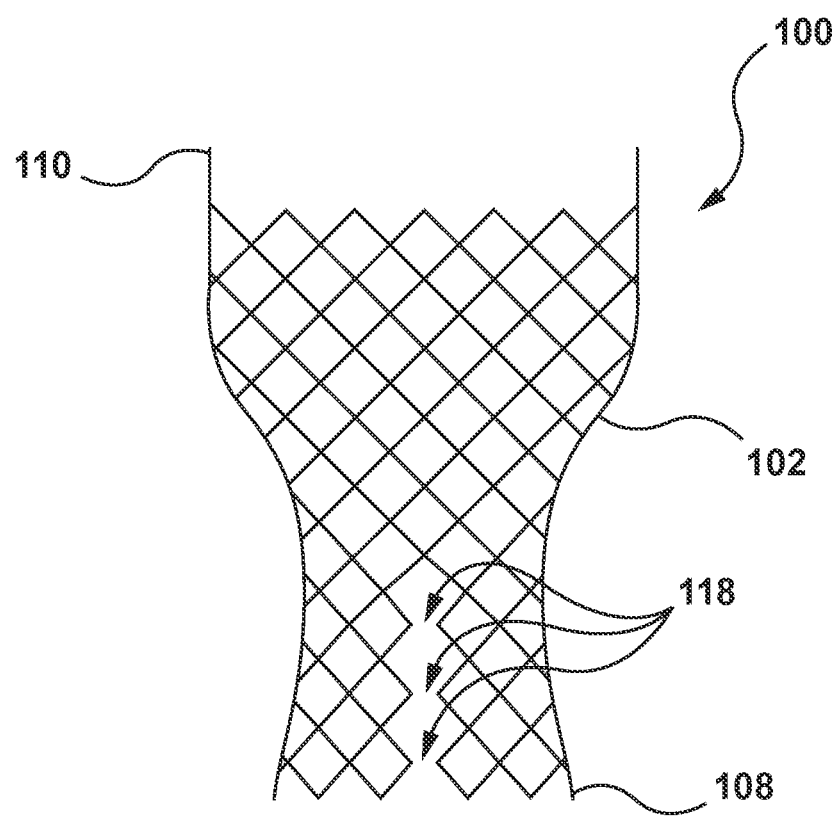
FIG. 5C depicts the valve prosthesis of FIG. 4, wherein a plurality of connection points have been fractured to form a "zipper down" opening in the frame of the valve prosthesis.

In an example shown in FIG. 5C, three (3) connection points 118 have been fractured at the inflow end 108 of the frame 102 of the valve prosthesis 100, forming a "zippered down" opening. The fracturing of three (3) to four (4) consecutive longitudinally aligned connection points 118 at the inflow end 108 and/or the outflow end 110 of the frame 102 will allow radial expansion of the frame 102 to permit a valve-in-valve replacement procedure to be utilized. While fracturing of the longitudinally aligned connection points 118 is shown at the inflow end 108, this is by way of example and not limitation. The fracturing of connection points 118 may occur at the inflow end 108, the outflow end 110, or at any connection point 118 there between. Further, while shown with a single set of three (3) longitudinally aligned connection points 118 being fractured, this too is by way of example and not limitation. It will be understood that the fracturing procedure may be utilized to fracture a single connection point 118, or to fracture more than one connection point 118 at any location on the frame 102 in any combination. The goal of the fracturing procedure is to fracture and separate enough connection points 118 to permit the frame 102 to radially expand to permit placement and expansion of a new valve prosthesis 100 therein. It will be understood that not every connection point 118 need be fractured to achieve a large diametrical expansion of the frame 102 to permit a valve-in-valve replacement.

When fracturing of the desired connection points 118 is complete, the system 301 is removed. Fracturing of the desired connection points 118 of the frame 102 of the deployed valve prosthesis 100 permits the frame 102 to radially expand. Radial expansion of the deployed frame 102 may be required such that the deployed frame 102 may receive, for example, a replacement valve prosthesis.

Figure 6:
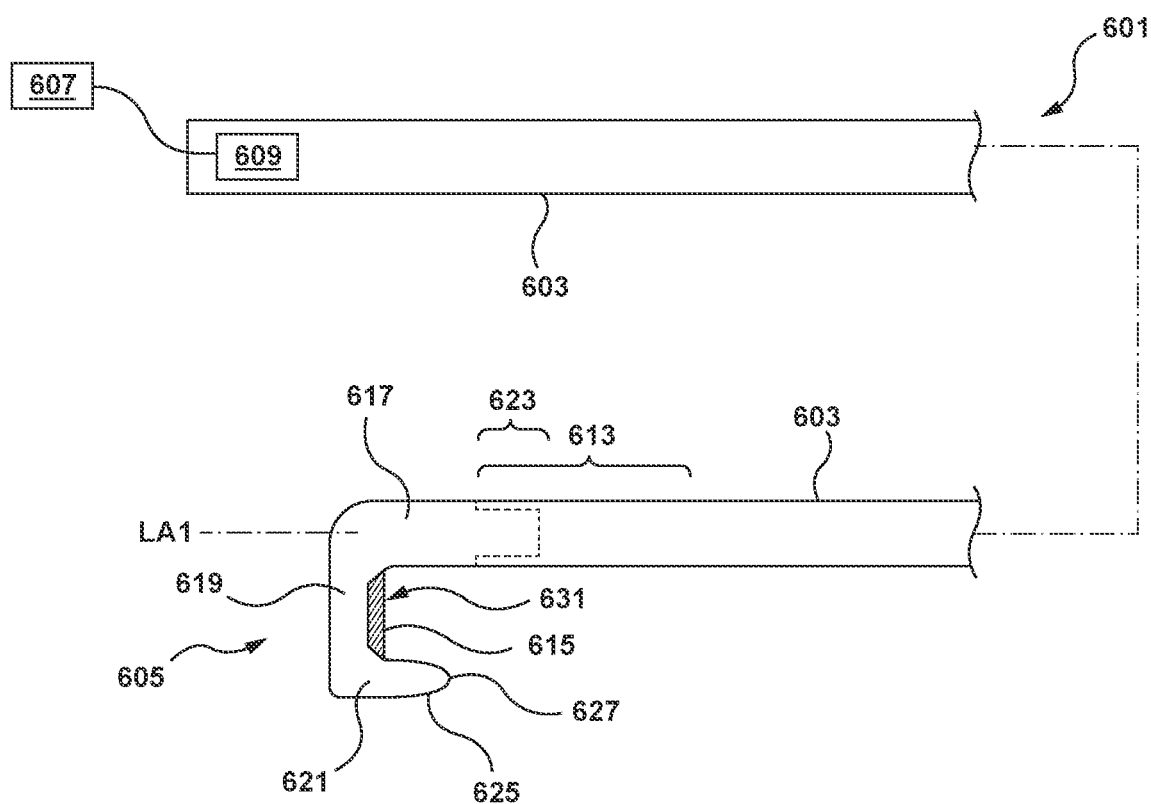
FIG. 6 depicts a side view illustration of a tip assembly according to another embodiment hereof.
Figure 7:
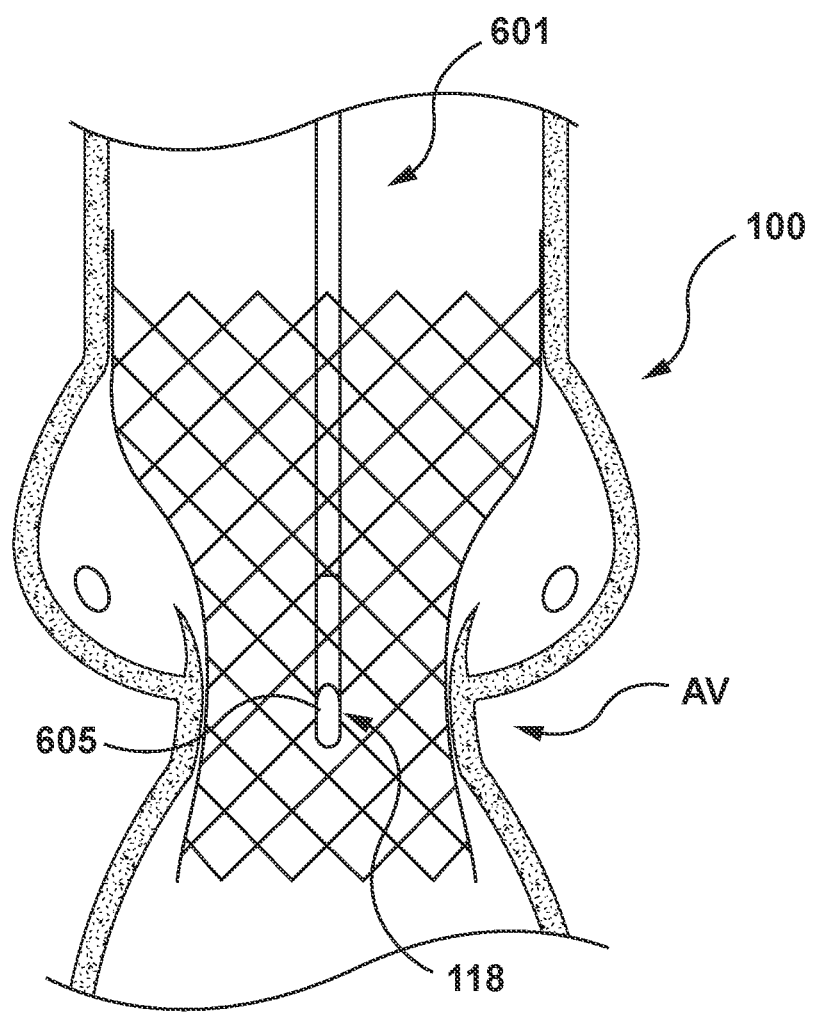
FIG. 7 depicts a sectional cut-away illustration of a heart and the tip assembly of FIG. 6 positioned at a desired connection point to be fractured of a frame of a deployed valve prosthesis.
Figure 8:
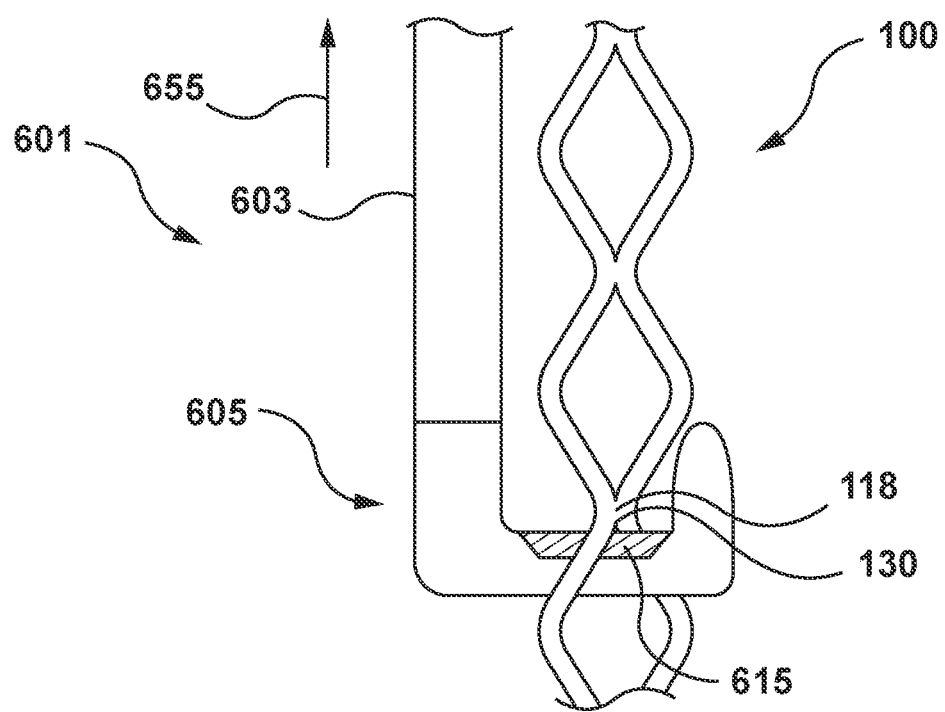
FIG. 8 depicts a close-up perspective illustration of the tip assembly of FIG. 6, wherein the tip assembly is adjacent to and in contact with the desired connection point of the frame of the deployed valve prosthesis.

FIGS. 6-8 illustrate a system 601 for fracturing a frame of a deployed valve prosthesis, such as the frame 102 of the valve prosthesis 100 previously described herein, with ultrasonic vibration according to another embodiment hereof. The system 601 includes a shaft 603, a tip assembly 605, an ultrasonic electric generator 607, and an ultrasonic transducer 609. The shaft 603, the ultrasonic electric generator 607, and the ultrasonic transducer 609 are similar to the shaft 303, the ultrasonic electric generator 307, and the ultrasonic transducer 309. Therefore, construction and alternatives of the shaft 603, the ultrasonic electric generator 605, and the ultrasonic transducer 609 will not be repeated. However, in the embodiment of FIGS. 6-8, the system 601 is equipped with an alternative tip assembly 605.

The tip assembly 605 according to an embodiment hereof is shown in FIGS. 6-8. The tip assembly 605 includes a sharpened edge 615, a first segment 617, a second segment 619, and a third segment 621. A proximal portion 623 of the tip assembly 605 is coupled to a distal portion 613 of the shaft 603. More precisely, the proximal portion 623 of the tip assembly 605 is located on the first segment 617. The tip assembly 605 is configured to translate ultrasonic vibration of the tip assembly 605 onto the frame 102 of the deployed valve prosthesis 100. The tip assembly 605 may be constructed of materials similar to the tip assembly 305 of FIGS. 3-5A. The tip assembly 605 may be coupled to the shaft 603 similar to the manner in which the tip assembly 305 is coupled to the shaft 303 of FIGS. 3-5.

The first segment 617 includes a first longitudinal axis LA1, as shown in FIG. 6. The second segment 619 of the tip assembly 605 extends radially outward from, or generally transverse to the first segment 617. The third segment 621 extends proximally from the second segment 619 such that the third segment 621 is generally parallel to and radially outward from the first longitudinal axis LA1. Stated another way, the third segment 621 is generally parallel to and radially spaced apart from the first segment 617 and the first longitudinal axis LA1. The third segment 621 is configured such that the third segment 621 will not damage tissue during delivery of the tip assembly 605 to the deployed valve prosthesis 100 or during fracturing of the frame 102, as described below. Accordingly, in the embodiment of FIGS. 6-8, the third segment 621 includes a conical portion 625 and a rounded or atraumatic tip 627 at a proximal portion thereof. While the tip assembly 605, and more precisely the first segment 617, the second segment 619, and the third segment 621 have been described herein as a single component, this is not meant to limit the design and the first segment 617, the second segment 619, and the third segment 621 may be separate components coupled together by methods such as but not limited adhesives, welding, or other coupling methods as appropriate. Further, while the first segment 617, the second segment 619, and the third segment 621 are each illustrated in FIGS. 6-8 with a generally circular cross-section, this is by way of example and not limitation. It will be understood that other cross-sectional shapes may be utilized as previously described with respect to the tip assembly 305 of FIGS. 3-5A.

In the embodiment of FIGS. 6-8, the sharpened edge 615 is formed on a proximal facing surface 631 of the tip assembly 605. The sharpened edge 615 is configured to focus or concentrate motion or ultrasonic vibration of the tip assembly 605 along the first longitudinal axis LA1 of the first segment 617 onto the desired connection point 118 of the frame 102, to fracture the desired connection point 118, as described below. The sharpened edge 615 may be formed by methods similar to the methods described for forming the sharpened edge 315 of FIGS. 3-5A.

As shown in FIG. 7, the tip assembly 605 of the system 601 is advanced to the site of a deployed valve prosthesis 100, in this example at the site of a native aortic valve AV, and brought into a position adjacent to the connection point 118 to be fractured.

The third segment 621 of the tip assembly 605 is manipulated radially outward through the cell 112 of the frame 102 that is adjacent to an inflow facing surface 130 of the connection point 118 to be fractured. More precisely, the tip assembly 605 is moved radially outward through the cell 112 to position the sharpened edge 615 adjacent the inflow facing surface 130 of the desired connection point 118 to be fractured.

When the sharpened edge 615 is positioned proximal of and adjacent to the desired connection point 118, the system 601 is proximally retracted to position the sharpened edge 615 of the second segment 619 in contact with the inflow facing surface 130 of the desired connection point 118, as shown in FIG. 8, which omits a portion of the frame 102 of the valve prosthesis 100 for clarity.

Next, the shaft 603 is proximally retracted to maintain a constant force in the proximal direction, indicated in FIG. 8 by the arrow 655, on the shaft 603 and the tip assembly 605. The force in the proximal direction (indicated by the arrow 655) keeps the sharpened edge 615 in contact with the desired connection point 118. The proximal force (indicated by the arrow 655) is seen as a tension force by the shaft 603.

When the proximal force (indicated by the arrow 653) is holding the sharpened edge 615 against the proximal facing surface 130 of the desired connection point 118, the ultrasonic electric generator 607 and the ultrasonic transducer 609 are activated to fracture the desired connection point 118 as previously described with respect to the tip assembly 305 of FIGS. 3-5A.

Figure 9:
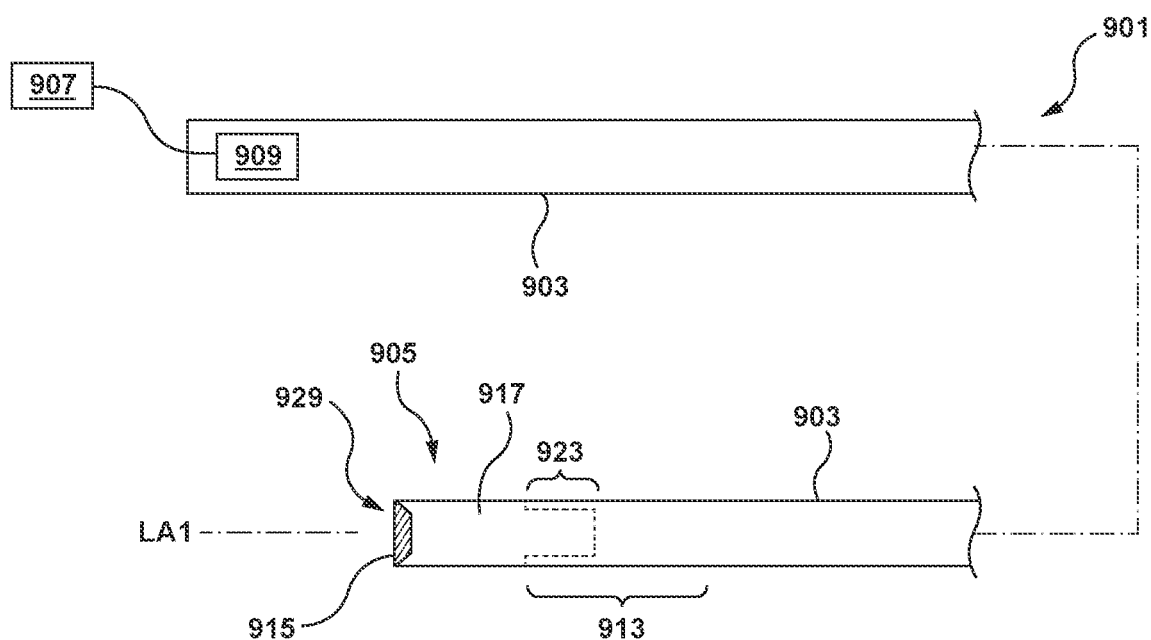
FIG. 9 depicts a side view illustration of a tip assembly according to another embodiment hereof.
Figure 10:
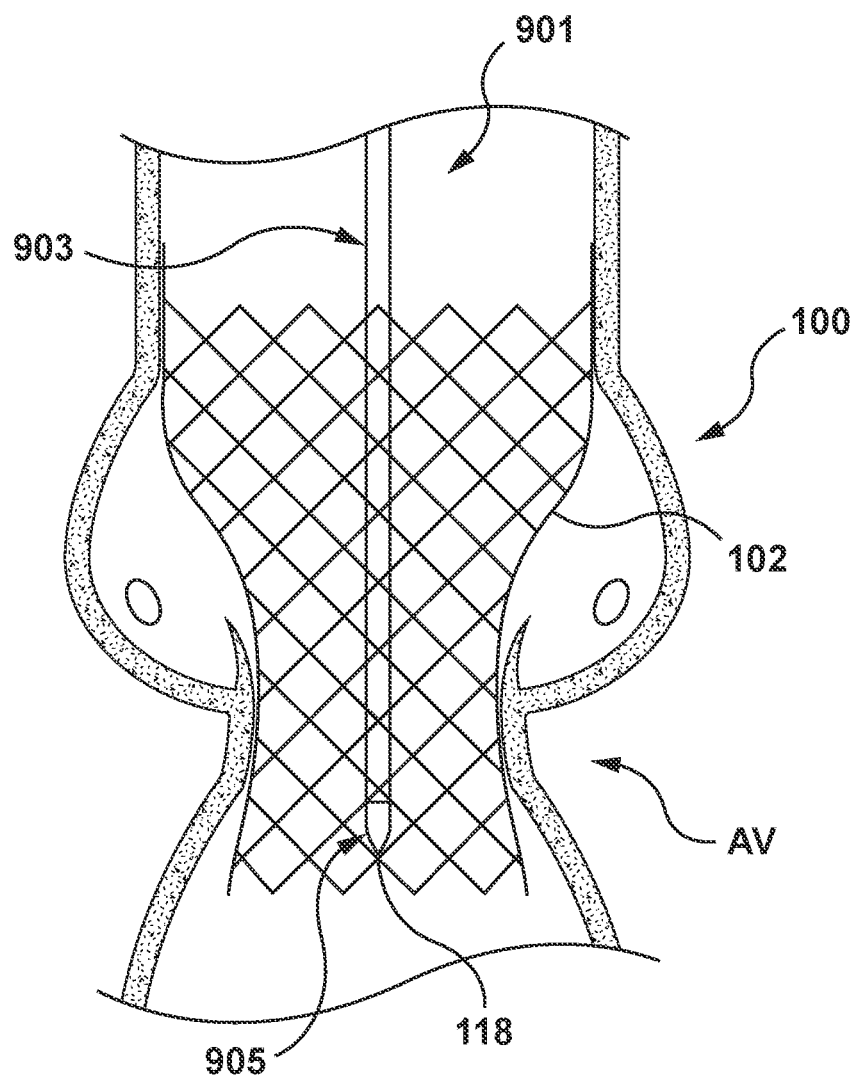
FIG. 10 depicts a sectional cut-away illustration of a heart and the tip assembly of FIG. 9 positioned at a desired connection point to be fractured of a frame of a deployed valve prosthesis.
Figure 11:
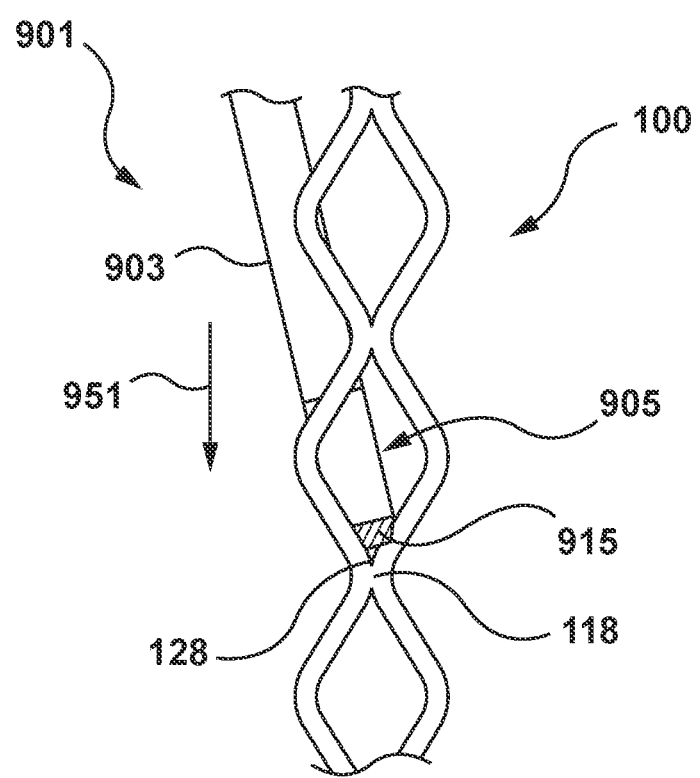
FIG. 11 depicts a close-up perspective illustration of the tip assembly of FIG. 9, wherein the tip assembly is adjacent to and in contact with the desired connection point of the frame of the valve prosthesis.

A system 901 for fracturing a frame of a deployed valve prosthesis, such as the frame 102 of the valve prosthesis 100 previously described herein, with ultrasonic vibration according to yet another embodiment hereof is shown in FIGS. 9-11. The system 901 includes a shaft 903, a tip assembly 905, an ultrasonic electric generator 907, and an ultrasonic transducer 909. The shaft 903, the ultrasonic electric generator 907, and the ultrasonic transducer 909 are similar to the shaft 303, the ultrasonic electric generator 307, and the ultrasonic transducer 309 and therefore are not described in detail with respect to FIGS. 9-12.

The tip assembly 905 according to yet another embodiment hereof is shown in FIGS. 9-11. The tip assembly 905 includes a sharpened edge 915 and a first segment 917. The tip assembly 905 is configured to translate ultrasonic vibration to the sharpened edge 915 and onto the frame 102 of the deployed valve prosthesis 100. Referring to FIG. 9, the first segment 917 includes a proximal portion 923 coupled to a distal portion 913 of the shaft 903 as previously described with respect to the tip assembly 305 of FIGS. 3-5. The sharpened edge 915 is disposed on a distal facing surface 929 of the first segment 917 of the tip assembly 905. The sharpened edge 915 is similar to the sharpened edge 315 previously described herein.

FIG. 10 shows the tip assembly 905 of the system 901 having been advanced to the site of a deployed valve prosthesis 100 and brought into a position adjacent the desired connection point 118 to be fractured.

The tip assembly 905 is manipulated to place the sharpened edge 915 in contact with the distal facing surface 128 of the connection point 118 to be fractured, as shown in FIG. 11.

The shaft 903 is distally advanced to provide a constant force in the distal direction, indicated in FIG. 11 by the arrow 951, to keep the sharpened edge 915 in contact with the desired connection point 118.

When the sharpened edge 915 held against the connection point 118 by the constant force in the distal direction (indicated by the arrow 951), the ultrasonic electric generator 907 and the ultrasonic transducer 909 are activated to fracture the desired connection point 118 as previously described herein.

Figure 12:
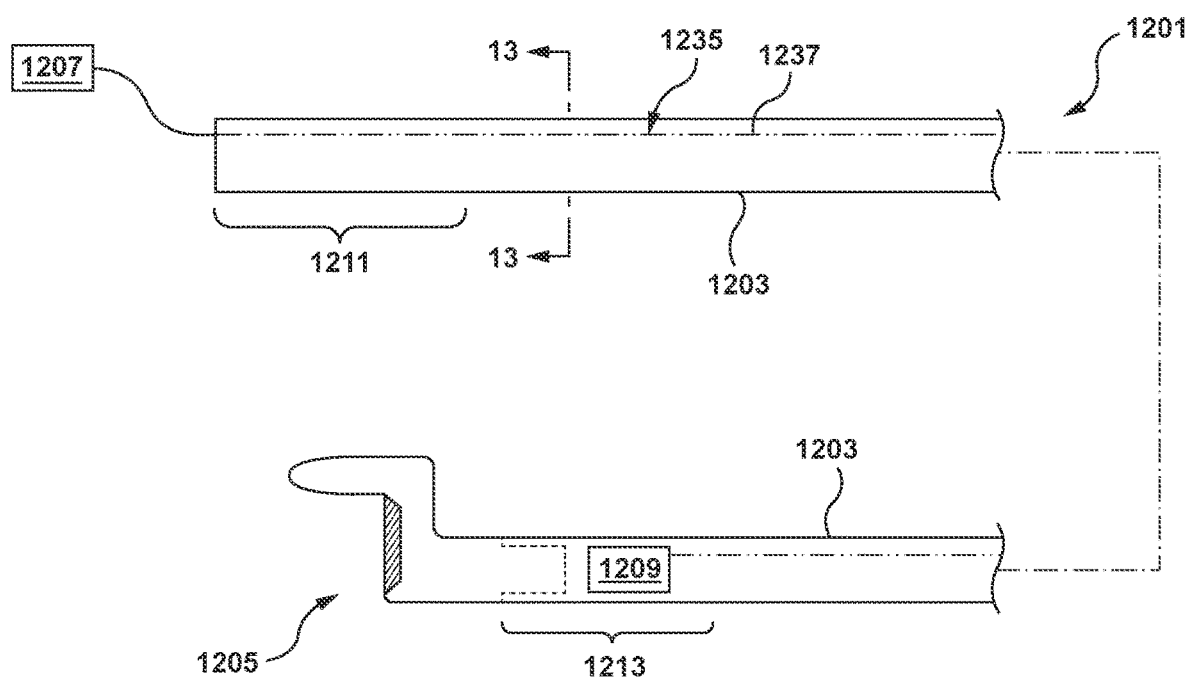
FIG. 12 depicts a side view illustration of a system according to another embodiment hereof, wherein the system includes an ultrasonic transducer disposed at a distal portion of a shaft of the system.
Figure 13:
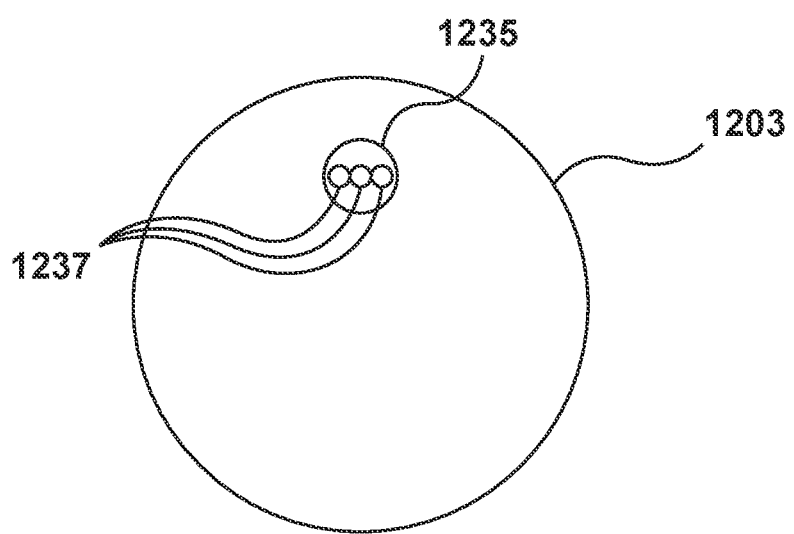
FIG. 13 depicts a cross-sectional illustration of the shaft of the system, taken along the line 13-13 of FIG. 12.

FIGS. 12-13 show a system 1201 for fracturing a frame of a deployed valve prosthesis in accordance with another embodiment hereof. The system 1201 includes a shaft 1203, a tip assembly 1205, an ultrasonic electric generator 1207, and an ultrasonic transducer 1209. The tip assembly 1205, the ultrasonic electric generator 1207, and the ultrasonic transducer 1209 are similar to the tip assembly 305, the ultrasonic electric generator 307, and ultrasonic transducer 309 previously described herein, except the ultrasonic transducer 1209 is disposed at a distal portion 1213 of the shaft 1203, as shown in FIG. 12. Therefore similar construction, operation, and alternatives of the tip assembly 1205, the ultrasonic electric generator 1207, and the ultrasonic transducer 1209 will not be repeated.

The shaft 1203 of the system 1201 is a generally tubular shape and includes a proximal portion 1211 and a distal portion 1213. The distal portion 1213 of the shaft 1203 is coupled to the ultrasonic transducer 1209 as described below. The shaft 1203 is configured to translate ultrasonic vibration generated by the ultrasonic transducer 1239 to the tip assembly 1205, as described below. The tip assembly 1205 is coupled to the distal portion 1213 of the shaft 1203 as previously described for the shaft 303 and the tip assembly 305 of FIGS. 3-5A. Although described herein as a single component, it will be understood that the shaft 1203 may include multiple components and be formed of similar materials as previously described with respect to the shaft 303 of FIGS. 3-5.

The shaft 1203 further includes a wire lumen 1235 extending from the proximal portion 1211 to the distal portion 1213 of the shaft 1203. More specifically, the wire lumen 1235 extends from the proximal portion 1211 of the shaft 1203 to the ultrasonic transducer 1209. The wire lumen 1235 is configured to retain at least one wire 1237, as best shown in FIG. 13, which is a cross-sectional view of the shaft 1203 taken at line 13-13 of FIG. 12. In the embodiment of FIG. 13, the shaft 1203 includes three (3) wires within the wire lumen 1235. In an embodiment, the three (3) wires include a positive, hot, or supply wire, a neutral, negative, or return wire, and a ground, earth, or protection wire. The at least one wire 1237 extends from the ultrasonic transducer 1209 proximally to the proximal portion 1211, and may extend to the ultrasonic electric generator 1207 such that the ultrasonic electric generator 1207 is electrically coupled to the ultrasonic transducer 1209. Alternatively, a suitable electrical connection may connect the ultrasonic electric generator 1207 with the at least one wire 1237 at the proximal portion 1211 of the shaft 1203. Although the wire lumen 1235 is depicted in FIG. 13 with a circular cross-section, this is by way of example and not limitation, and other cross-sectional configurations of the wire lumen 1235, including elliptical, oval, crescent shaped, or other configurations suitable for the purposes described herein may be utilized. Further, while shown in FIG. 13 with three (3) wires 1237 within the wire lumen 1235, this, too, is by way of example and not limitation, and more or fewer wires 1237 may be utilized.

The ultrasonic transducer 1209 is coupled to the distal portion 1213 of the shaft 1203. The ultrasonic transducer 1209 is configured to receive an electrical signal from the ultrasonic electric generator 1207 via the at least one wire 1237, and convert the electrical signal to ultrasonic vibration or motion. The ultrasonic transducer 1209 is further configured to translate the ultrasonic vibration to the distal portion 1213 of the shaft 1203 to which the ultrasonic transducer 1209 it is coupled. The ultrasonic transducer 1209 may be coupled to the distal portion 1213 of the shaft 1203 by methods such as, but not limited to adhesives, welding, clamping, or other coupling methods as appropriate.

The interaction of the various components of the system 1201 are similar to the interaction of components of the system 301 previously described with respect to FIGS. 3-5A, except that the ultrasonic vibration is generated by the ultrasonic transducer 1209 at the distal portion 1213 of the shaft 1203.

Figure 14:
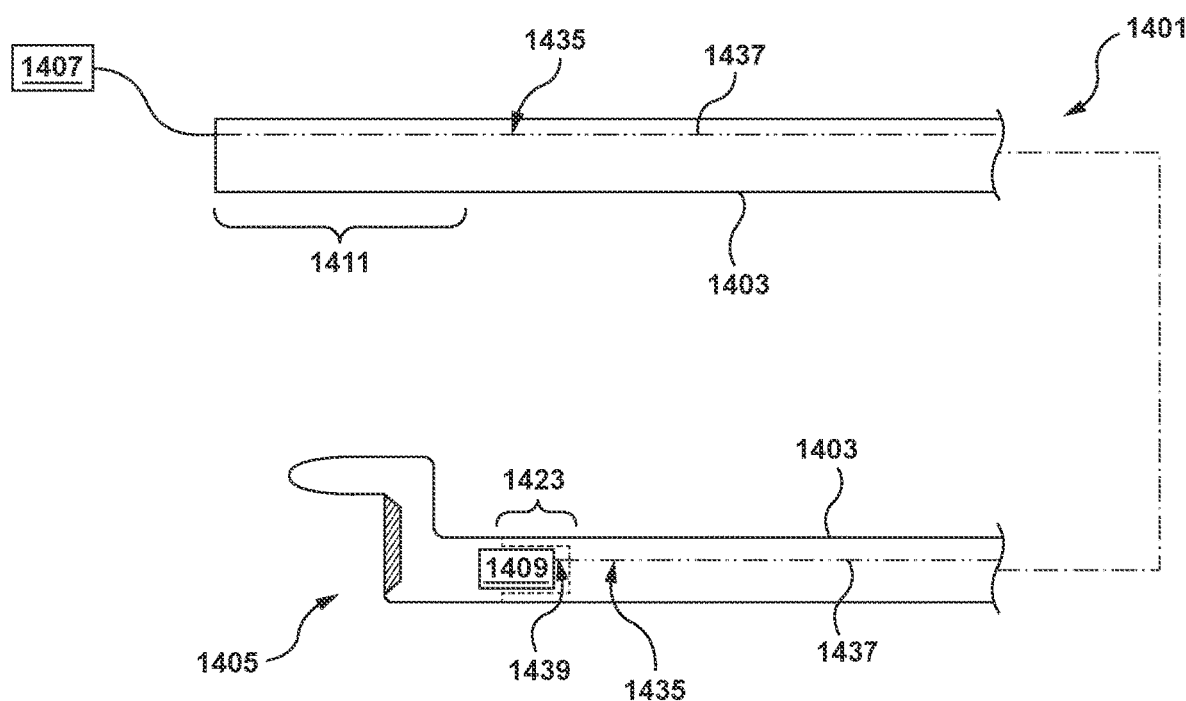
FIG. 14 depicts a side view illustration of a system according to yet another embodiment hereof, wherein the system includes an ultrasonic transducer disposed at a tip assembly of the system.

A system 1401 for fracturing a frame of a deployed valve prosthesis in accordance with another embodiment hereof is shown in FIG. 14. The system 1401 includes a shaft 1403, a tip assembly 1405, an ultrasonic electric generator 1407, and an ultrasonic transducer 1409. The shaft 1403, the tip assembly 1405, the ultrasonic electric generator 1407, and the electronic ultrasonic transducer 1409 are similar to the shaft 1203, the tip assembly 1205, the ultrasonic generator 1207, and the ultrasonic transducer 1209 previously described with FIGS. 12-13, except in the embodiment of FIG. 14, the ultrasonic transducer 1209 is disposed at and coupled to a proximal portion 1423 of the tip assembly 1405, as described below. Therefore, similar construction and alternatives will not be repeated.

The shaft 1403 includes a wire lumen 1435 extending from the proximal portion 1411 to the distal portion 1413 of the shaft 1403. The tip assembly 1405 includes a wire lumen 1439 longitudinally aligned with the wire lumen 1435 of the shaft 1403 such that the wire lumen 1435 and the wire lumen 1439 form a continuous lumen extending from the proximal portion 1411 of the shaft 1403 to the proximal portion 1423 of the tip assembly 1405. The wire lumen 1435 of the shaft 1403 and the wire lumen 1439 of the tip assembly 1405 are each configured to retain at least one wire 1437. The at least one wire 1437 extends from the ultrasonic transducer 1409 proximally to the proximal portion 1411, and may extend to the ultrasonic electric generator 1407 to electrically couple the ultrasonic transducer 1409 to the ultrasonic electric generator 1407. Alternatively, a suitable electrical connection may connect the ultrasonic electric generator 1407 with the at least one wire 1437 at the proximal portion 1411 of the shaft 1403. The ultrasonic transducer 1409 is configured to receive an electrical signal from the ultrasonic electric generator 1407 via the at least one wire 1437, and convert the electrical signal to ultrasonic vibration. The ultrasonic transducer 1409 is further configured to translate the ultrasonic vibration to the tip assembly 1405. The ultrasonic transducer 1409 may be coupled to the proximal portion 1423 of the tip assembly 1405 by methods such as, but not limited to adhesives, welding, clamping, or other coupling methods as appropriate.

The interaction of the various components of the system 1401 are similar to the interaction of components of the system 301 previously described herein.

Figure 15A:
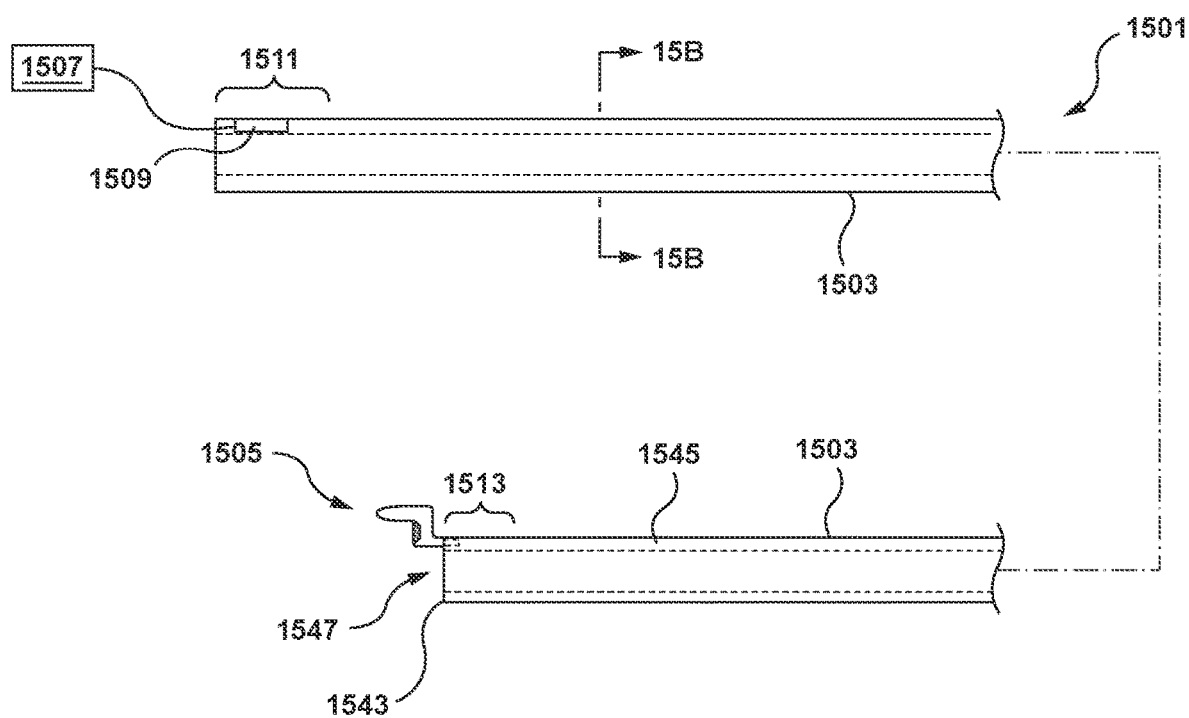
FIG. 15A depicts a side view illustration of a system according to another embodiment hereof, wherein the system includes a catheter shaft.
Figure 15B:
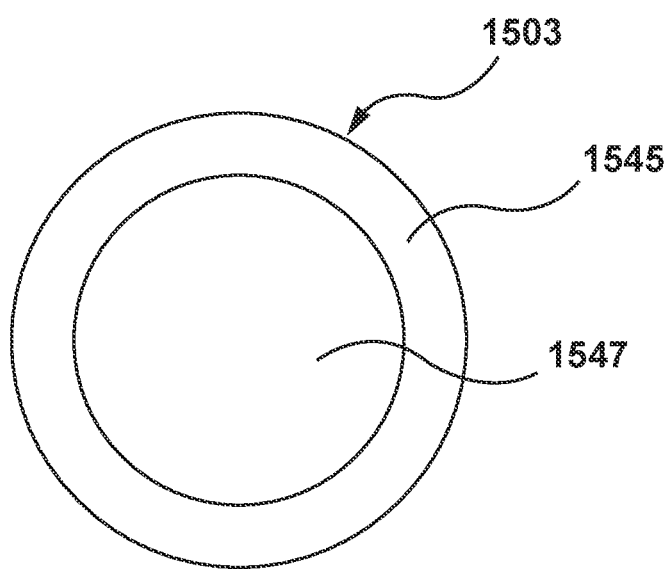
FIG. 15B depicts a cross-sectional illustration of the shaft of the system, taken along the line 15B-15B of FIG. 15A.

A system 1501 for fracturing a frame of a deployed valve prosthesis, such as the frame 102 of the valve prosthesis 100 previously described herein, with ultrasonic vibration according to yet another embodiment hereof is shown in FIGS. 15A-15B. The system 1501 includes a shaft 1503, a tip assembly 1505, an ultrasonic electric generator 1507, and an ultrasonic transducer 1509. The tip assembly 1505, the ultrasonic electric generator 1507, and the ultrasonic transducer 1509 are similar to the tip assembly 305, the ultrasonic electric generator 307, and the ultrasonic transducer 309 and therefore are not described in detail with respect to FIGS. 9-12.

The shaft 1503 is a flexible catheter shaft with a generally tubular shape. The shaft 1503 includes a proximal portion 1511, a distal portion 1513, a proximal end 1541, and a distal end 1543. The shaft 1503 further includes a shaft wall 1545 and a lumen 1547 extending from the proximal end 1541 to the distal end 1543, as shown in FIGS. 15A and 15B. The lumen 1547 is sized and configured to receive auxiliary medical devices such as, but not limited to a guidewire. In the embodiment of FIGS. 15A-15B, the proximal portion 1511 is coupled to the ultrasonic transducer 1509 and the distal portion 1513 is coupled to the tip assembly 1505. The shaft 1503 is configured to translate movement or vibration from the proximal portion 1511 to the distal portion 1513. More specifically, the shaft 1503 is configured to translate ultrasonic vibration from the ultrasonic transducer 1509 coupled to the proximal portion 1511 to the tip assembly 1505 coupled to the distal portion 1513. Although the shaft 1503 is described herein as a single component, this is by way of example and not limitation, and the shaft 1503 may include components such as, but not limited to a proximal shaft, a distal shaft, a handle, or other components suitable for the purposes described herein. The shaft 1503 may be constructed of materials such as, but not limited to stainless steel, titanium, tungsten, tantalum, or other materials suitable for the purposes of the present disclosure. In an alternative embodiment, the shaft 1503 may be coated or surrounded by a plastic or polymer-based material such as, but not limited to Polyurethane (e.g. Peliethane©, Elasthane™, Texin®, Tecothane®), polyamide polyether block copolymer (e.g. Pebax®, nylon 12), polyethylene, or other materials suitable for the purposes of the present disclosure.

Although the embodiment of FIGS. 15A-15B is shown with the tip assembly 1505 coupled to the wall 1545 of the shaft 1503 at a distal portion 1513 thereof, this is by way of example and not limitation. In another embodiment, the tip assembly 1505 may be coupled to other locations of the distal portion 1513 of the shaft 1503 such as, but not limited to an outer surface of the shaft 1503, an inner surface of the shaft 1503, or any other location suitable for the purposes described herein. For example, in another embodiment, the shaft may include a second lumen disposed within the wall of the shaft and configured to receive a second shaft there through. A tip assembly may be coupled to a distal portion of the second shaft extending distally from the shaft. The second shaft is configured to translate ultrasonic vibration from the shaft to the tip assembly. In an embodiment, the second shaft may be slidably and/or rotatably disposed within the second lumen such that the tip assembly may be distally advanced, proximally retracted, and/or radially rotated relative to the shaft.

The interaction of the various components of the system 1501 are similar to the interaction of components of the system 301 previously described herein.

Figure 16:
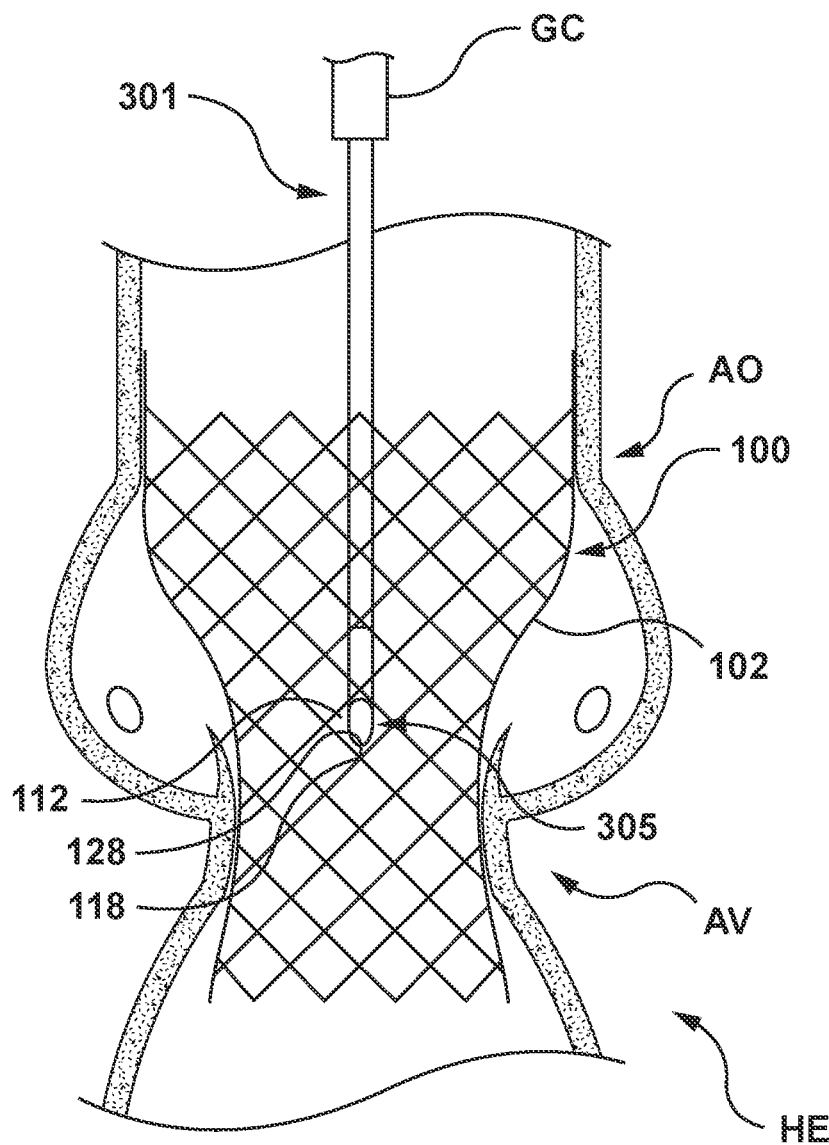
FIG. 16 is a sectional cut-away illustration of an aorta of a heart illustrating a method step of using the system of FIG. 3 to fracture a frame of a deployed aortic valve prosthesis in accordance with an embodiment hereof, wherein a tip assembly is positioned adjacent the frame of the deployed valve prosthesis.

FIGS. 16-20 are sectional cutaways views of a heart HE illustrating a method for fracturing the frame 102 of the deployed heart valve prosthesis 100 using the system 301 of FIGS. 3-5A in accordance with an embodiment hereof. FIG. 16 shows the system 301 having been introduced into the vasculature via a percutaneous entry point, e.g., the Seldinger technique, and tracked through the vasculature and into the aorta AO of the heart HE with the tip assembly 305 advanced into proximity or apposition with the valve prosthesis 100 at the site of a native aortic valve AV. Intravascular access to the aortic valve AV may be achieved via a percutaneous access site to femoral venous access to the aorta AO or other known access routes. A guide catheter GC may be used with the system 301 to minimize intravascular trauma during introduction, tracking and positioning of the tip assembly 305 at the desired location. The system 301 has been advanced distally to place the tip assembly 305 adjacent with the cell 112 that is adjacent the outflow facing surface 128 of the desired connection point 118 of the frame 102 that is to be fractured.

Figure 17:
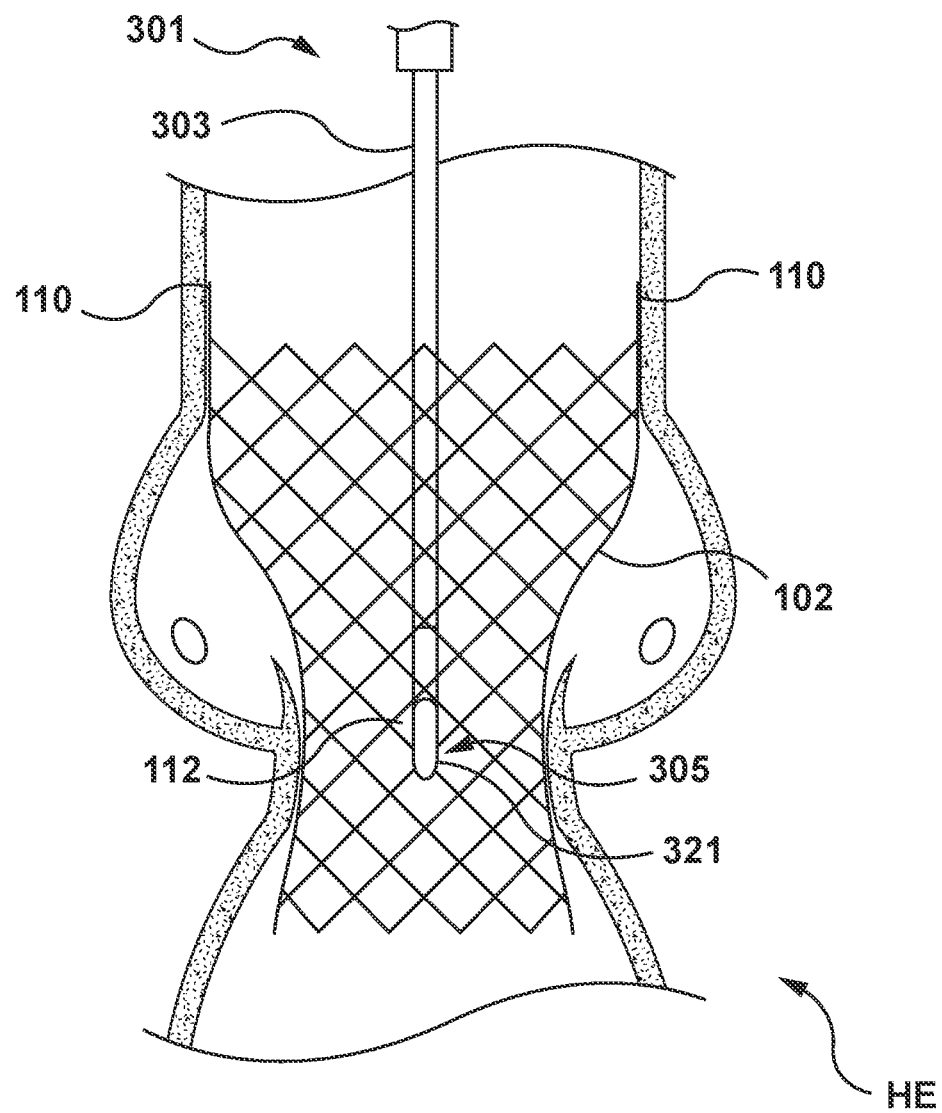
FIG. 17 is a sectional cutaway illustration of the heart illustrating a method step of using the system of FIG. 3 to fracture the frame of the deployed valve prosthesis, wherein a sharpened edge of the tip assembly is adjacent a desired connection point to be fractured.

In a next step, the system 301, and more precisely the shaft 303 is manipulated to move the third segment 321 of the tip assembly 305 radially outward through the cell 112 that is adjacent the outflow facing surface 128 of the desired connection point 118 (obscured from view in FIG. 17 by the tip assembly 305) to be fractured, as shown in FIG. 17. Movement of the third segment 321 through the cell 112 of the frame 102 positions the sharpened edge 315 (obscured from view in FIG. 17 by the tip assembly 305) of the tip assembly 305 adjacent to the connection point 118 to be fractured.

Figure 18:
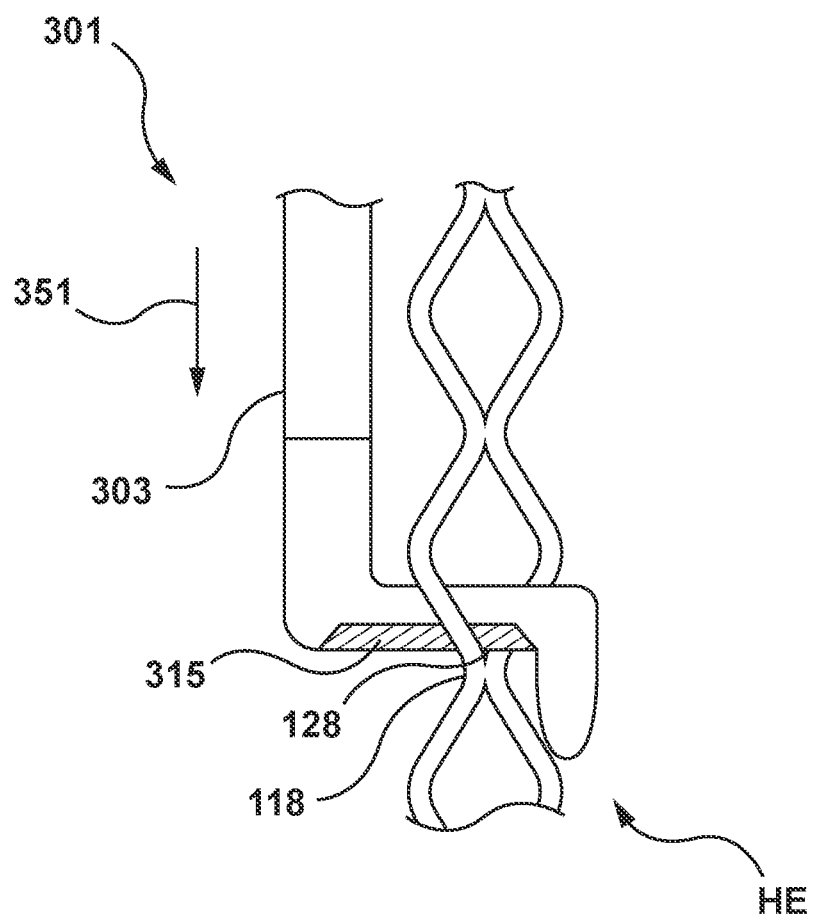
FIG. 18 is a close-up perspective illustration of tip assembly illustrating a method step of using the system of FIG. 3 to fracture the frame of the deployed valve prosthesis, wherein the sharpened edge of the tip assembly is in contact with the desired connection point to be fractured.

With reference to FIG. 18, the shaft 303 of the system 301 is distally advanced to place the sharpened edge 315 of the tip assembly 305 in contact with the distal facing surface 128 (in relation to the valve prosthesis 100) of the desired connection point 118 to be fractured.

When the sharpened edge 315 is in contact with the desired connection point 118, the shaft 303 is distally advance to apply a longitudinal force in the distal direction, indicated by the arrow 351, on the shaft 303 and the tip assembly 305 to keep or hold the sharpened edge 315 in contact with the desired connection point 118.

Figure 19:
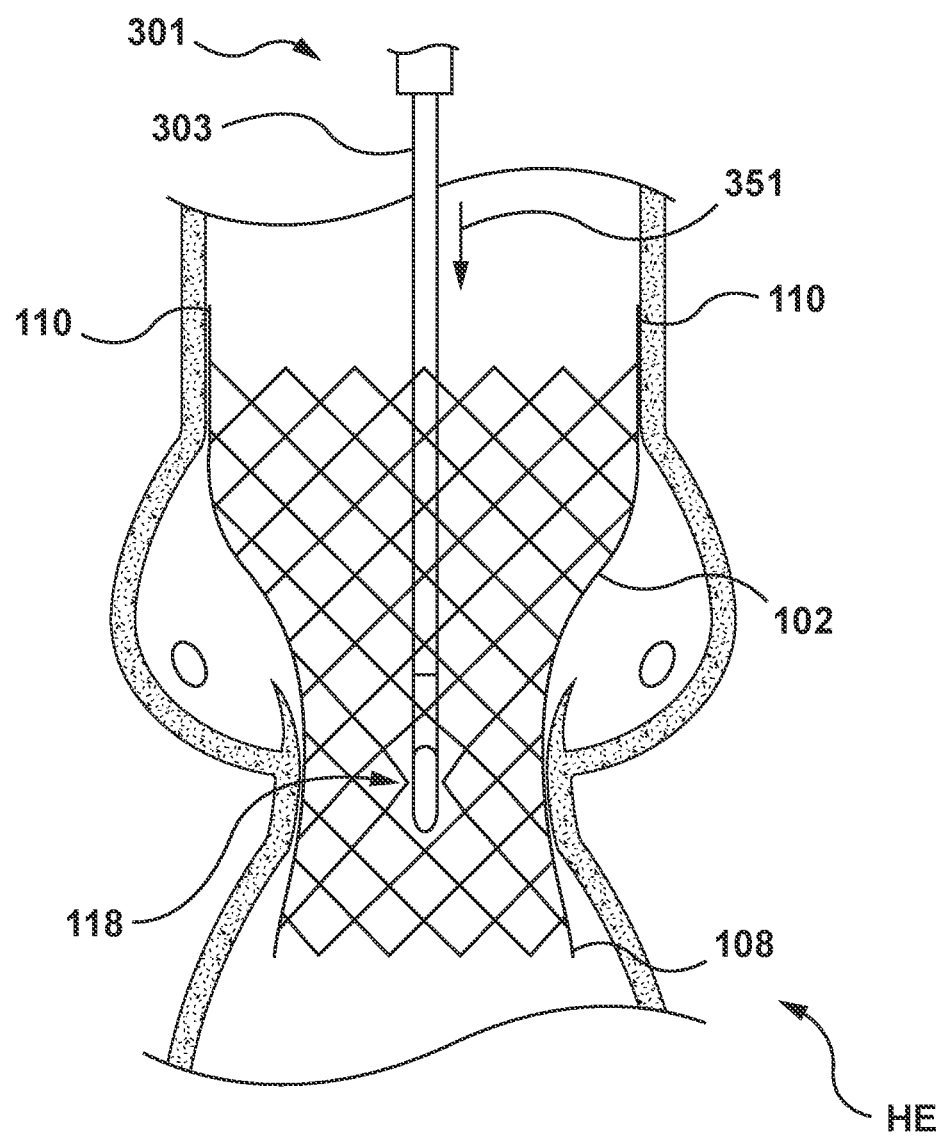
FIG. 19 is a sectional cutaway illustration of the heart illustrating a method step of using the system of FIG. 3 to fracture the frame of the deployed valve prosthesis, wherein the sharpened edge has fractured or separated the desired connection point.

When the sharpened edge 315 is held in contact with the desired connection point 118 by the distal force 351, the ultrasonic electric generator 307 and the ultrasonic transducer 309 (not visible in FIGS. 16-20) are activated. The ultrasonic electric generator 307 and the ultrasonic transducer 309 remain activated and the longitudinal distal force 351 is maintained until the desired connection point 118 of the frame 102 fractures or fails, as shown in FIG. 19.

When the desired connection point 118 has fractured, the ultrasonic electric generator 307 and the ultrasonic transducer 309 may be deactivated, and the longitudinal distal force 351 released.

The method steps may be repeated for the next desired connection point 118 to be fractured.

As previously described with respect to FIGS. 3-5C, one or more of the connection points 118 of the frame 102 are fractured at desired locations to permit the desired radial expansion of the frame 102 to permit a valve-in-valve replacement. Accordingly, connection points 118 may be fractured at and inflow end 108 of the frame 102, at an outflow end 110 of the frame 102, at any other desired location of the frame 102, and in any combination.

Figure 20:
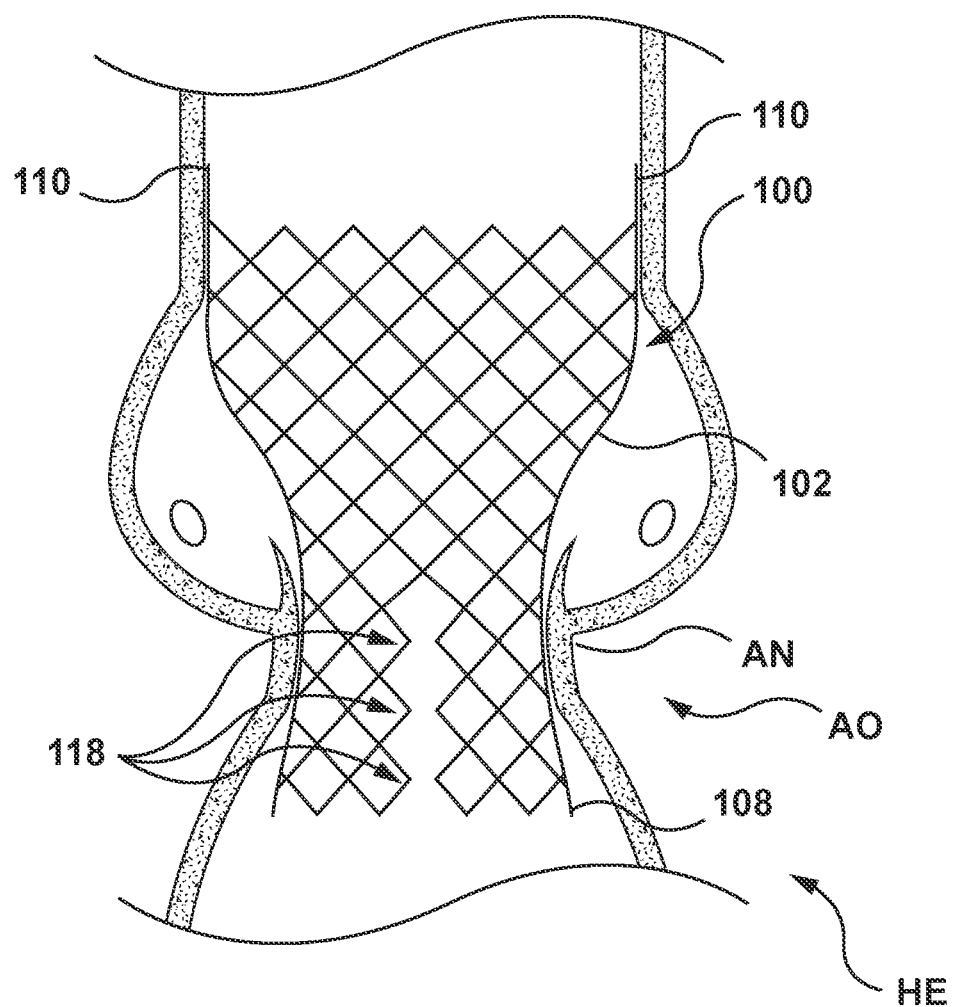
FIG. 20 is a sectional cutaway illustration of the heart illustrating a method step of using the system of FIG. 3 to fracture the frame of the deployed valve prosthesis, wherein the system has been removed to leave the fractured valve prosthesis.

When all the desired connection points 118 have been fractured, the system 301 may be removed. FIG. 20 illustrates the frame 102 of the deployed heart valve prosthesis 100, wherein three (3) connection points 118 in a longitudinal alignment at the inflow end 108 of the frame 102 have been fractured, thus permitting a portion of the frame 102 to radially expand and form a "zippered down" opening within an annulus AN of the native aortic valve AV. The system 301 is now removed and the deployed valve prosthesis 100, or more precisely the frame 102 of the deployed valve prosthesis 100 is ready to receive a new valve prosthesis therein in a valve-in-valve replacement procedure.

While the method of FIGS. 16-20 is described with the system 301, this is by way of example and not limitation, and the method may also be utilized with other embodiments of the system including the system 601 of FIGS. 6-8, the system 901 of FIGS. 9-11, the system 1201 of FIGS. 12 and 13, the system 1401 of FIG. 14, and the system 1501 of FIGS. 15A-15B.

Further, while the method of FIGS. 16-20 is described with the tip assembly 305, this too is by way of example and not limitation, and it will be understood that a similar method may be employed with the alternated tips assembly configurations including the tip assembly 605 of FIGS. 6-8, the tip assembly 905 of FIGS. 9-11, the tip assembly 1405 of FIG. 14, and the tip assembly 1505 of FIG. 15A. When utilized with the tip assembly 605 of FIGS. 6-8, the sharpened edge 615 of the tip assembly 605 is placed in contact with a proximal facing surface of the connection point 118 to be fractured and the shaft 603 is proximally retracted to apply the longitudinal force to maintain contact between the sharpened edge 615 and the desired connection point 118.

Although the method has been described with respect to the fracturing of a frame 102 of a deployed aortic heart valve prosthesis 100, it will be understood that the method may be utilized with other prostheses, and at other locations, such as deployed heart valve prostheses at the mitral valve, the tricuspid valve, or the pulmonary valve.

Figure 21:
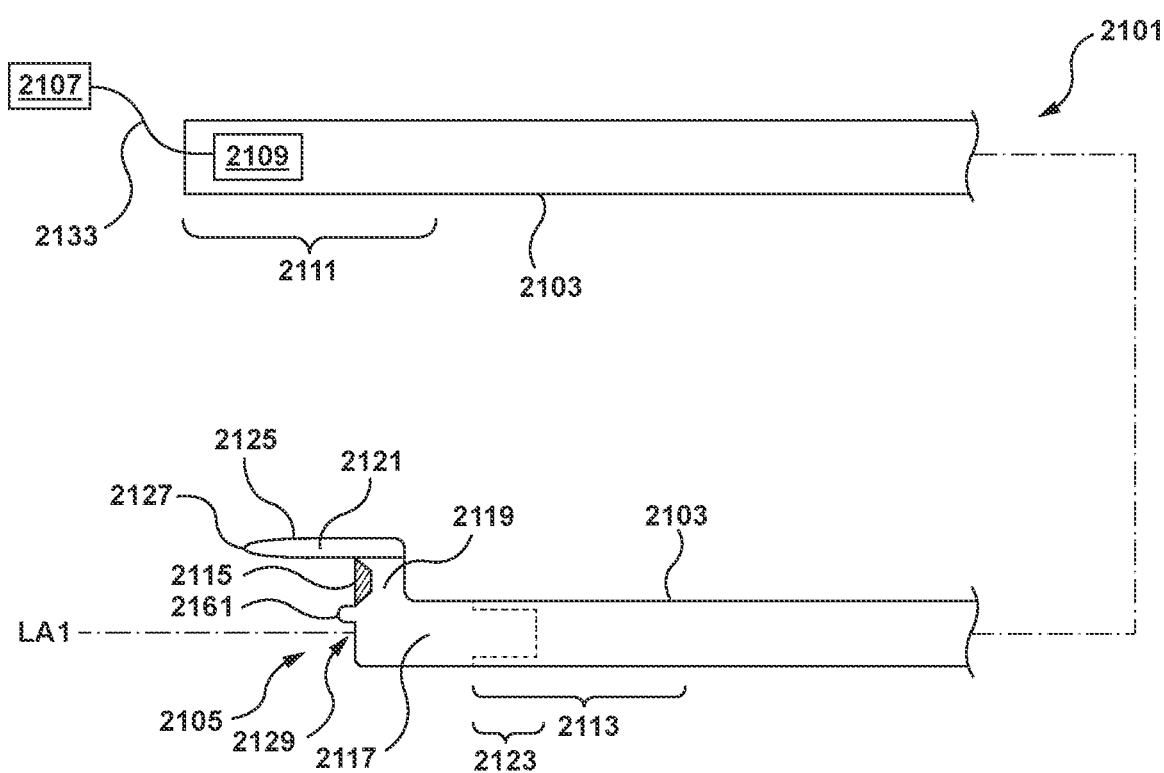
FIG. 21 depicts a side view illustration of a system according to an embodiment hereof, wherein a tip assembly of the system includes a safety bumper and a flat, rounded tip according to an embodiment hereof.
Figure 22:
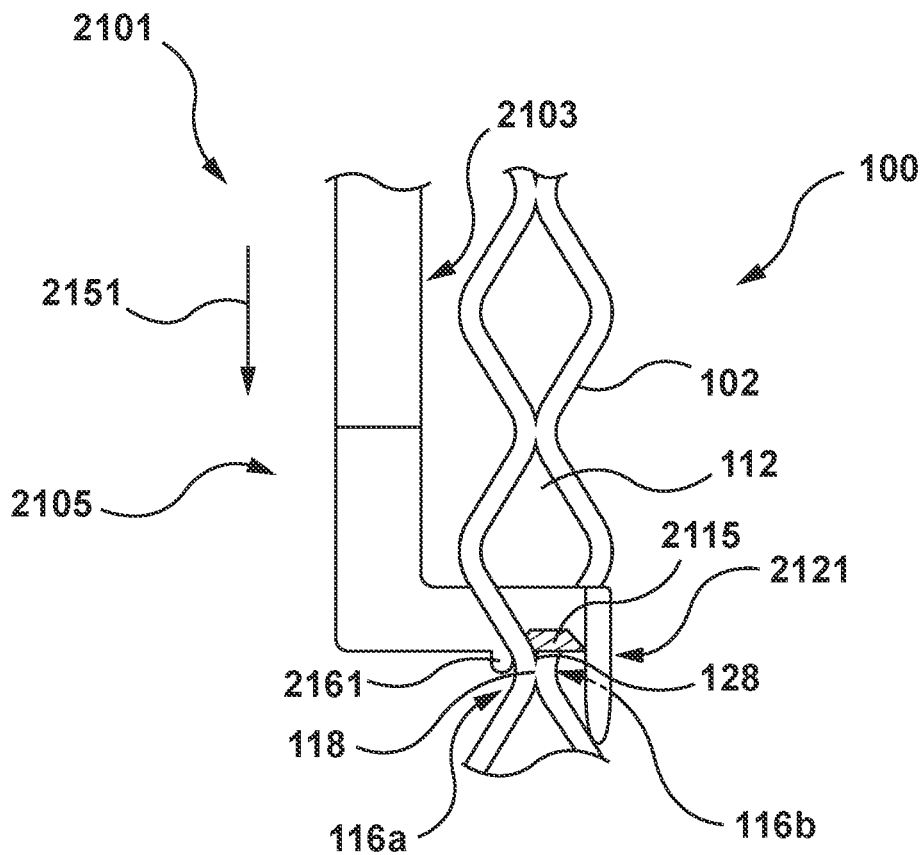
FIG. 22 depicts a close-up perspective illustration of the tip assembly of the system of FIG. 21, wherein the tip assembly is adjacent to and in contact with the desired connection point of the frame of the deployed valve prosthesis.

A system 2101 for fracturing a frame of a deployed valve prosthesis, such as the frame 102 of the valve prosthesis 100 previously described herein, with ultrasonic vibration according to yet another embodiment hereof is shown in FIGS. 21 and 22. The system 2101 includes a shaft 2103 having a proximal portion 2111 and a distal portion 2133, a tip assembly 2105, an ultrasonic electric generator 2107, and an ultrasonic transducer 2109. The ultrasonic electric generator 2107 is electrically coupled to the ultrasonic transducer 2109 by a connection 2133. The shaft 2103, the ultrasonic electric generator 2107, the ultrasonic transducer 2109, and the connection 2133 are similar to the shaft 303, the ultrasonic electric generator 307, the ultrasonic transducer 309, and the connection 333, respectively, and therefore are not described in detail with respect to FIGS. 21 and 22. A proximal portion 2123 of the tip assembly 2105 is coupled to the distal portion 2133 of the shaft 2103. The tip assembly 2105 includes a sharpened edge 2115, a first segment 2117, a second segment 2119, and a third segment 2121. The tip assembly 2105 is similar to the tip assembly 305 previously described with respect to FIGS. 3-5, except that in the embodiment of FIGS. 21 and 22, the second segment 2119 includes a safety bumper 2161, and the third segment 2121 includes a flat portion 2125 with a rounded or atraumatic tip 2127 at a distal portion thereof.

In the embodiment of FIGS. 21 and 22, the flat portion 2125 of the third segment 2121 of the tip assembly 2105 has a generally flat or planar shape with an oblong or rectangular cross-section. The flat portion 2125 is configured to be pressed against adjacent tissue to locate a desired connection 118 to be fractured without damaging the adjacent tissue. Further, the flat portion 2125 is configured to protect against deep tissue damage during fracturing of the desired connection 118.

In the embodiment of FIGS. 21 and 22, the safety bumper 2161 is disposed on a distal facing surface 2129 of the tip assembly 2105. The safety bumper 2161 is disposed radially inward relative to a sharpened edge 2115. The safety bumper 2161 is configured to prevent the third segment 2121 from damaging tissue during fracturing of the desired connection 118 of the frame 102 of the deployed valve prosthesis 100. More precisely, when the sharpened edge 2115 is disposed against the desired connection 118, the third segment 2121 is disposed radially outward from the desired connection 118 and the safety bumper 2161 is disposed radially inward of the desired connection 118. Stated another way, the desired connection 118 is sandwiched between the third segment 2121 and the safety bumper 2161 as best shown on FIG. 22.

When the ultrasonic electric generator 2107 and the ultrasonic transducer 2109 are activated, the safety bumper 2161, disposed radially inward from and adjacent to the desired connection 118 prevents the tip assembly 2105 from moving radially outward, thereby further preventing the third segment 2121 from moving radially outward and damaging adjacent arterial tissue. A constant force in the distal direction, indicated in FIG. 22 by an arrow 2151, is maintained on the shaft 2103 to keep the sharpened edge 2115 in contact with the desired connection point 118.

Figure 23:
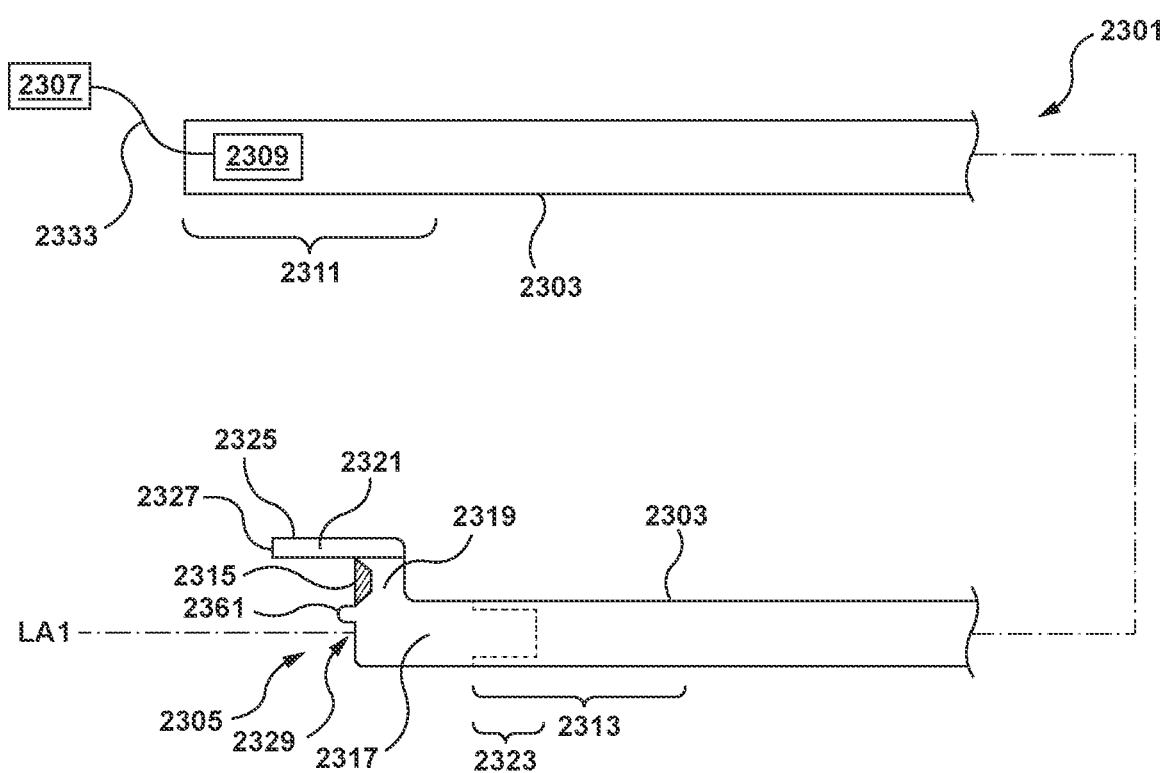
FIG. 23 depicts a side view illustration of a system according to an embodiment hereof, wherein a tip assembly of the system includes a safety bumper and a flat, rectangular tip according to an embodiment hereof.
Figure 24:
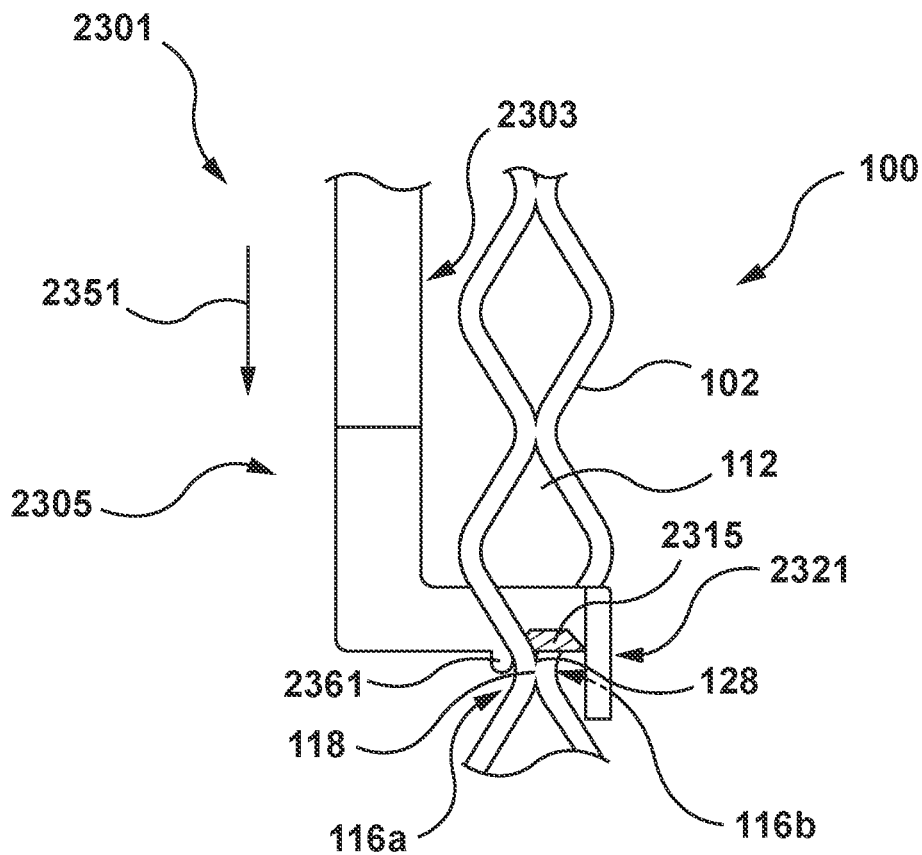
FIG. 24 depicts a close-up perspective illustration of the tip assembly of the system of FIG. 23, wherein the tip assembly is adjacent to and in contact with the desired connection point of the frame of the deployed valve prosthesis.

FIGS. 23 and 24 show a system 2301 for fracturing a frame of a deployed valve prosthesis, such as the frame 102 of the valve prosthesis 100 previously described herein, with ultrasonic vibration according to yet another embodiment hereof. The system 2301 includes a shaft 2303 having a proximal portion 2311 and a distal portion 2313, a tip assembly 2305, an ultrasonic electric generator 2307, and an ultrasonic transducer 2309. The ultrasonic electric generator 2307 is electrically coupled to the ultrasonic transducer 2309 by a connection 2333. The shaft 2303, the ultrasonic electric generator 2307, the ultrasonic transducer 2309, and the connection 2333 are similar to the shaft 303, the ultrasonic electric generator 307, the ultrasonic transducer 309, and the connection 333, respectively, and therefore are not described in detail with respect to FIGS. 23 and 24. A proximal portion 2323 of the tip assembly 2305 is coupled to the distal portion 2313 of the shaft 2303. The tip assembly 2305 includes a sharpened edge 2315, a first segment 2517, a second segment 2519, and a third segment 2321. The tip assembly 2305 is similar to the tip assembly 2105 previously described with respect to FIGS. 21 and 22, except that in the embodiment of FIGS. 23 and 24 a third segment 2321 includes a flat portion 2325 with a square tip 2327 at a distal portion thereof.

In the embodiment of FIGS. 23 and 24, the flat portion 2325 of the third segment 2321 of the tip assembly 2305 has a rectangular shape with a rectangular or oblong cross-section. The flat portion 2325 is configured to be pressed against adjacent tissue to locate a desired connection 118 to be fractured without damaging the adjacent tissue. Further, the flat portion 2325 is configured to protect against deep tissue damage during fracturing of the desired crown 118. The tip 2327 has a square shape, flat, or blunt distal end.

In the embodiment of FIGS. 23 and 24, a safety bumper 2361 is similar to the safety bumper 2161 of the embodiment of FIGS. 21 and 22. Therefore, the safety bumper 2361 is not described in detail with respect to FIGS. 23 and 24. When the ultrasonic electric generator 2307 and the ultrasonic transducer 2309 are activated, the safety bumper 2361, disposed radially inward from and adjacent to the desired connection 118 prevents the tip assembly 2305 from moving radially outward, thereby further preventing the third segment 2321 from moving radially outward and damaging adjacent arterial tissue. A constant force in the distal direction, indicated in FIG. 24 by an arrow 2351, is maintained on the shaft 2303 to keep the sharpened edge 2315 in contact with the desired connection point 118.

A system 2501 for fracturing a frame of a deployed valve prosthesis, such as the frame 102 of the valve prosthesis 100 previously described herein, with ultrasonic vibration according to yet another embodiment hereof is shown in FIGS. 25-29. The system 2501 includes a shaft 2503, a tip assembly 2505, an ultrasonic electric generator 2507, and an ultrasonic transducer 2509. The ultrasonic electric generator 2507, and the ultrasonic transducer 2509 are similar to the ultrasonic electric generator 307 and the ultrasonic transducer 309 and therefore are not described in detail with respect to FIGS. 25-29. In the embodiment of FIGS. 25-29, the tip assembly 2505 includes a collapsed configuration for delivery and an expanded configuration for ultrasonic fracturing of the frame 102 of the valve prosthesis 100. The shaft 2503 is configured to permit transition of the tip assembly 2505 from the collapsed configuration of FIGS. 25 and 26 to the expanded configuration of FIG. 28 in situ, with the tensioning of a pull wire 2571, as described below.

The shaft 2503 is similar to the shaft 303 previously described with respect to FIGS. 3-5A, except that the shaft 2503 further includes a pull wire lumen 2535. The pull wire lumen 2535 extends the full length of the shaft 2503 to the tip assembly 2505. The pull wire lumen 2535 is sized to slidably receive the pull wire 2571 therein, as best shown in FIG. 27, which is a cross-sectional view of the shaft 2503 taken at line 27-27 of FIG. 25. In the embodiment of FIGS. 25-29, the shaft 2503 includes one (1) pull wire 2571 within the pull wire lumen 2535. Although the pull wire lumen 2535 is depicted in FIG. 26 with a circular cross-section, this is by way of example and not limitation, and other cross-sectional configurations of the pull wire lumen 2535, including elliptical, oval, or other configurations suitable for the purposes described herein may be utilized.

The pull wire 2571 is configured to transition the tip assembly 2505 from the collapsed configuration of FIGS. 25 and 26 to the expanded configuration of FIG. 28 when the pull wire is placed in tension, as described below. The pull wire 2571 includes a proximal end 2573 extending proximally from the shaft 2503. The pull wire extends distally from the proximal end 2573, through the pull wire lumen 2535 to a distal end 2575. The distal end 2575 of the pull wire 2571 is coupled to a third segment 2521 of the tip assembly 2505 as described below. In an embodiment, the pull wire 2571 is an elongate member formed of materials such as, but not limited to stainless steel or any other material suitable for the purposes described herein. In an embodiment, the pull wire 2571 may including a coating thereon to enhance slidability.

The tip assembly 2505 is configured to translate ultrasonic vibration of the tip assembly 2505 onto the frame 102 of the deployed valve prosthesis 100 to fracture the frame 102 of the deployed valve prosthesis 100, as previously described with respect to the tip assembly 305 of FIGS. 3-5C. Further, the tip assembly 2505 is configured to transition between the collapsed configuration and the expanded configuration. The tip assembly 2505 includes a sharpened edge 2515, a first segment 2517, a second segment 2519, and the third segment 2521. The first segment 2517, the second segment 2519, and the third segment 2521 are each individual components pivotably coupled to one another to provide articulation to transition the tip assembly 2505 from the collapsed configuration to the expanded configuration in situ, as described below.

In the embodiment of FIGS. 25-29, the first segment 2517 and the second segment 2519 each have a generally wishbone or "Y" shape. The third segment 2521 has a generally linear shape with a generally rectangular cross-section. The tip assembly 2505 may be constructed of materials such as, but not limited to stainless steel or other materials suitable for the purposes of the present disclosure. The tip assembly 2505 may be coupled to the shaft 2503, for example, and not by way of limitation by adhesives, welding, clamping, or other coupling methods as appropriate. While the tip assembly 2505 is shown coupled to the shaft 2503 in a particular coupling configuration, this is by way of example and not limitation, and it will be understood that other coupling configurations may be utilized. Further, while the first, second, and third segments 2517, 2519, and 2521 of the tip assembly 2505 have each been described with a specific shape, this is by way of example and not limitation, and the first, second, and third segments 2517, 2519, and 2521 may each have any number of alternative shapes to permit the tip assembly 2505 to transition between the collapsed and the expanded configurations.

More particularly, the first segment 2517 includes a generally wishbone or "Y" shape as best shown in FIG. 26, which is a top view illustration of the tip assembly 2505 in the collapsed configuration. As best shown in FIG. 29, which is an exploded view illustration of the tip assembly 2505 in the expanded configuration, the first segment 2517 further includes a first aperture 2577 and a first stop 2579 at a distal portion thereof. The first segment 2517 includes a first longitudinal axis LA1 (shown on FIG. 28). The second segment 2519 of the tip assembly 2505 includes a generally wishbone or "Y" shape. The second segment 2519 further includes a first aperture 2581 at a radially inward portion thereof, and a second aperture 2583 and a second stop 2585 at a radially outward portion thereof. The third segment 2521 includes a first aperture 2587 disposed at a distal portion thereof, and a coupling point 2599 disposed proximal of the first aperture 2587. In the embodiment of FIGS. 25-29, the first aperture 2581 of the second segment 2519 is co-located with the first aperture 2577 of the first segment 2517 and a first pivot pin 2589 is disposed through the co-located first apertures 2577 and 2581 to pivotably couple the second segment 2519 to the first segment 2517. The second segment 2519 is configured to pivot about the pivot pin 2589 between the collapsed configuration of FIG. 25 and the expanded configuration of FIG. 28. Similarly, the first aperture 2587 of the third segment 2521 is co-located with the second aperture 2583 of the second segment 2519 and a second pivot pin 2591 is disposed through the co-located apertures 2587 and 2583 to pivotably couple the third segment 2521 to the second segment 2519.

When the tip assembly 2505 is in the collapsed configuration, as best shown in FIG. 27, the second segment 2519 is pivotably disposed within a wishbone portion of the first segment 2517, and the third segment 2521 is pivotably disposed within a wishbone portion of the second segment 2519. The first, second, and third segments 2517, 2519, and 2521 are nested within one another and aligned generally parallel to the first longitudinal axis LA1.

Figure 28:
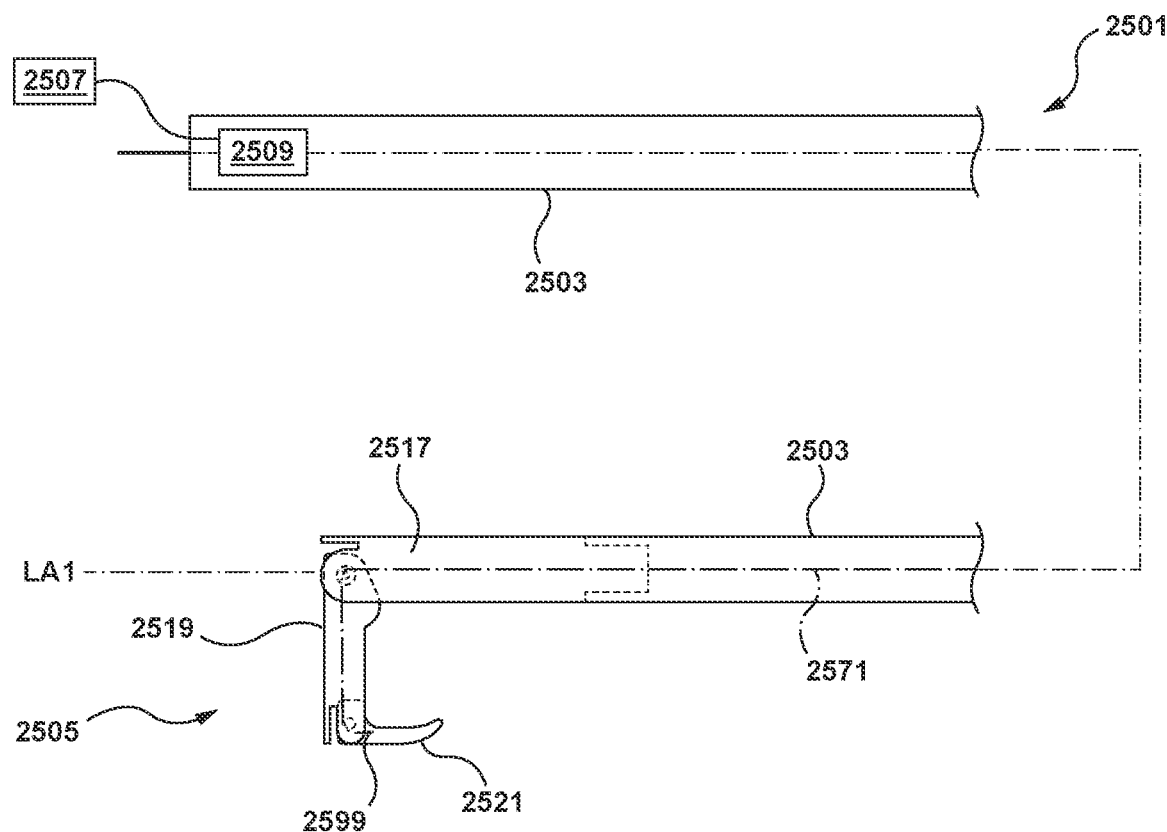
FIG. 28 depicts a side view illustration of the system of FIG. 25, wherein a tip assembly of the system is in an expanded configuration according to an embodiment hereof.
Figure 29:
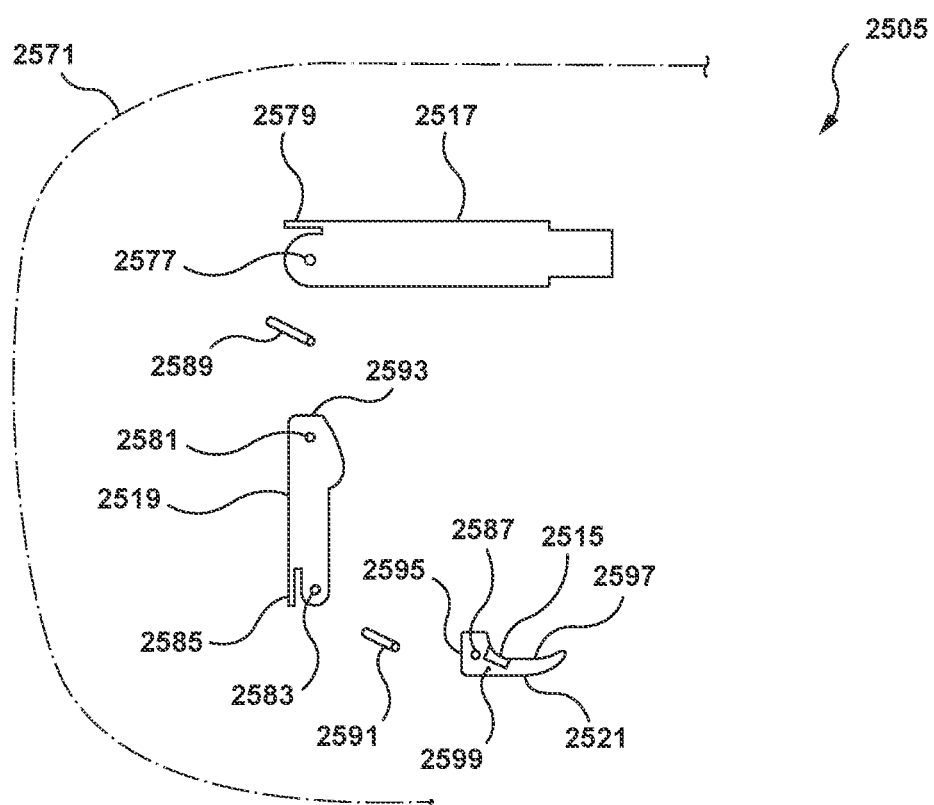
FIG. 29 depicts an exploded illustration of the tip assembly of FIG. 25.

When the tip assembly 2505 is in the expanded configuration, as shown in FIG. 28, the second segment 2519 of the tip assembly 2505 extends radially outward from, or generally transverse to the first segment 2517, and the third segment 2521 extends distally from the second segment 2519 such that the third segment 2521 is generally parallel to and radially outward from the first longitudinal axis LA1.

Figure 25:
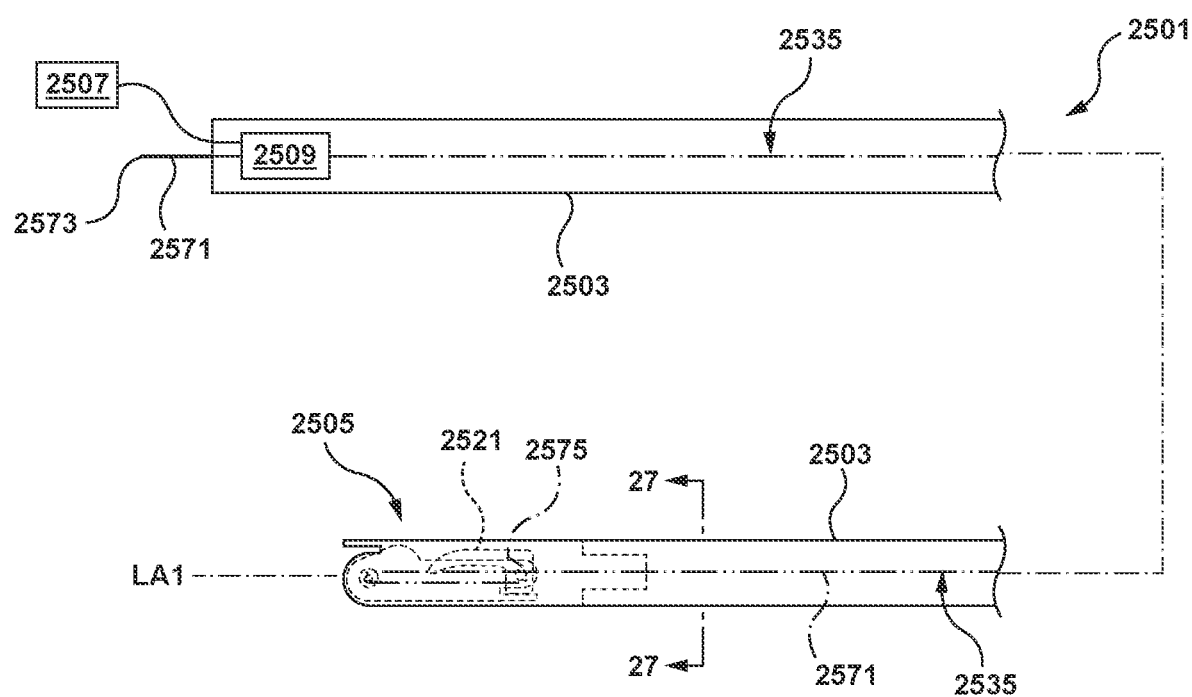
FIG. 25 depicts a side view illustration of a system according to an embodiment hereof, wherein a tip assembly of the system is in a collapsed configuration according to an embodiment hereof.
Figure 26:
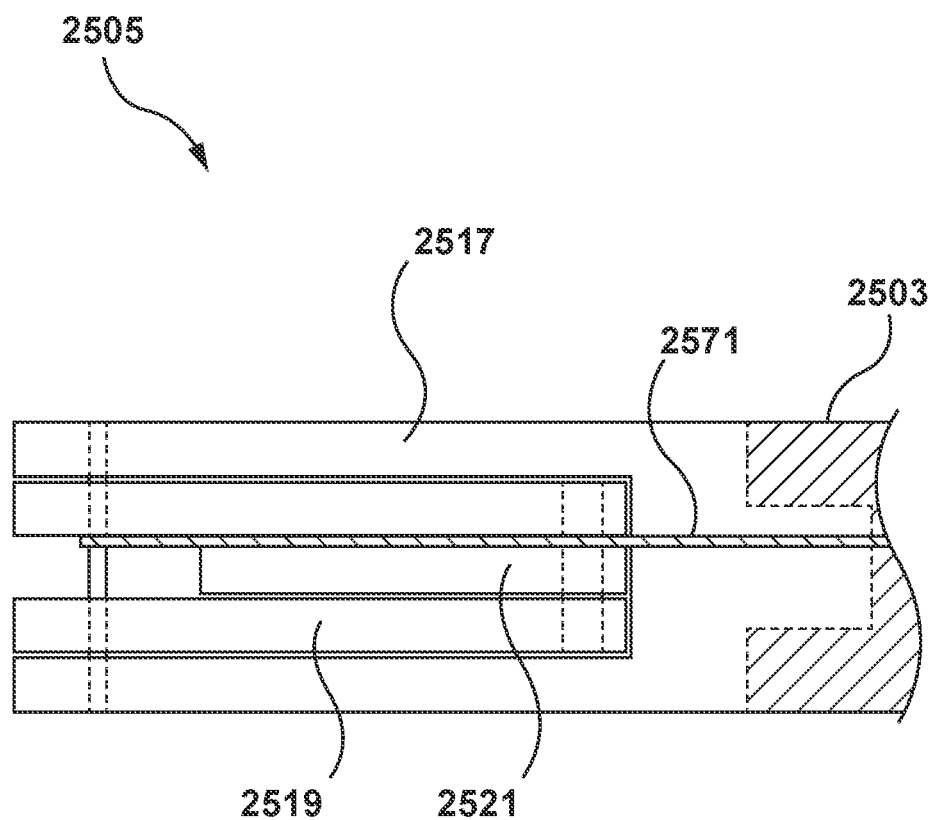
FIG. 26 depicts a top view illustration of the tip assembly of the system of FIG. 25, wherein the tip assembly is in the collapsed configuration.
Figure 27:
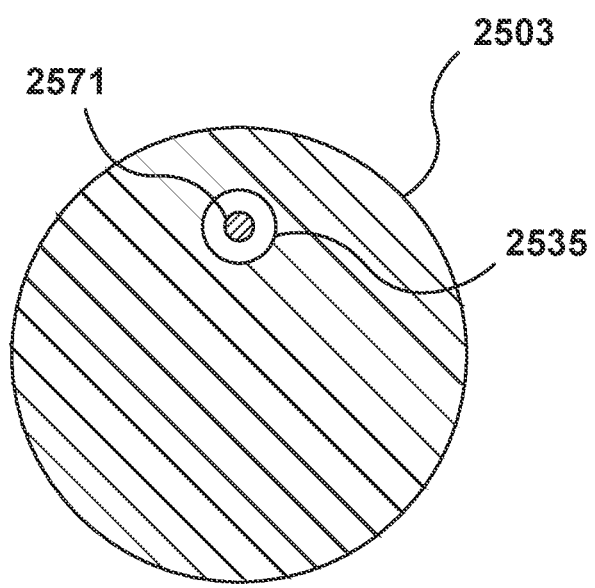
FIG. 27 depicts a cross-sectional illustration of a shaft of the system taken along the line 27-27 of FIG. 26.

In the embodiment of FIGS. 25-29, the first pivot pin 2589 and the second pivot pin 2591 are each biased such that the tip assembly 2505 is configured to return to the collapsed configuration of FIG. 25 when at rest. Accordingly, the first pivot pin 2589 is pivotably disposed within the first aperture 2577 of the first segment 2517 and disposed within and coupled to the first aperture 2581 of the second segment 2519 such that the second segment 2519 returns to the collapsed configuration of FIG. 25 when the pull wire 2571 is not in tension. Further, the second pivot pin 2591 is pivotably disposed within the second aperture 2583 of the second segment 2519 and is disposed within and coupled to the first aperture 2587 of the third segment 2521 such that the third segment 2521 returns to the collapsed configuration of FIG. 25 when the pull wire 2571 is not in tension. Biasing of the first and second pivot pins 2589, 2591 may be accomplished by springs or other biasing mechanisms as will be understood by persons knowledgeable in the pertinent art.

The first stop 2579 is configured to prevent the second segment 2519 from pivoting beyond a position generally curved traverse to the first segment 2517 when the tip assembly 2505 is in the expanded configuration. More precisely, when the tip assembly 2505 is in the expanded configuration, a radially inward end 2593 of the second segment 2519 contacts the first stop 2579 of the first segment 2517, when the second segment 2519 is generally transverse to the first segment 2517. Further, when the tip assembly 2505 is in the expanded configuration, a distal end 2595 of the third segment 2521 contacts the second stop 2585 of the second segment 2519 when the third segment 2521 is generally parallel to the first segment 2517. Stated another way, the first and second stops 2579 and 2585 each prevent the second and third segments 2519, 2521, respectively, from pivoting beyond or to a greater degree than the expanded configuration of FIG. 28.

In the embodiment of FIGS. 25-29, as best shown in FIG. 29, the sharpened edge 2515 is disposed on a radially inward facing surface 2597 of the third segment 2521 of the tip assembly 2505. The sharpened edge 2515 is similar to the sharpened edge 615 previously described with respect to FIGS. 6-8, except that the sharpened edge 2015 is disposed on a different surface of the tip assembly 2505. The sharpened edge 2515 is configured to focus or concentrate ultrasonic vibration or motion of the tip assembly 2505 to fracture a desired connection point of a frame of a deployed valve prosthesis as previously described.

Assembly of the articulating tip assembly 2505 will now be described with reference to FIGS. 28 and 29. The first aperture 2577 of the first segment 2517 is co-located with the first aperture 2581 of the second segment 2519. The first pivot pin 2589 is disposed through the first apertures 2577, 2581 to pivotably couple the second segment 2519 to the first segment 2517. The second aperture 2583 of the second segment 2519 is co-located with the first aperture 2595 of the third segment 2521. The second pivot pin 2591 is disposed through the co-located first and second apertures 2595, 2583 of the third segment to 2521 and the second segment 2519, respectively, to pivotably couple the third segment 2521 to the second segment 2519. The distal end 2575 of the pull wire 2571 is coupled to the third segment 2521 at the coupling point 2599, as best shown in FIG. 30. The distal end 2575 of the pull wire or 2521 may be coupled to the third segment 2521 by methods such as but not limited to adhesives, fusing, welding, tying, or any other method suitable for the purposes described herein. The pull wire 2571 extends distally from the coupling point 2599 of the third segment 2521 around a distal portion of the second pivot pin 2591. The pull wire 2571 then extends radially inward and around a distal portion of the first pivot pin 2589. Finally, the pull wire 2571 extends proximally within the pull wire lumen 2535 of the shaft 2503. The proximal end 2573 of the pull wire extends proximally from the shaft 303 such that the pull wire 2571 may be manipulated or placed into tension to transition the tip assembly 2505 from the collapsed configuration to the expanded configuration.

With reference to FIGS. 25-29, the interaction of the various components of the system 2501 will now be described to articulate, move, or transition the tip assembly 2505 from the collapsed configuration to the expanded configuration. When the system 2501 is in the collapsed configuration of FIG. 25 with the second segment 2519 nested within a portion of the first segment 2517, and the third segment 2521 nested within a portion of the second segment 2519, the pull wire 2571 is pulled in a proximal direction to place the pull wire 2571 into tension. Tension on the pull wire 2571 is translated to tension or pull at the distal end 2575 of the pull wire and translated to the connection point 2599 of the third segment 2521 coupled thereto. Accordingly, as the pull wire 2571 is placed into tension, the third segment 2521 and the pivotably coupled second segment 2519 of the tip assembly 2505 each pivot about their respective pivot pins 2591, 2589 to transition the tip assembly 2505 from the collapsed configuration of FIG. 25 to the expanded configuration of FIG. 28. More precisely, as the tip assembly 2505 transitions from the collapsed configuration to the expanded configuration, the second segment 2519 pivots about the first pivot pin 2589 in a radially outward direction, from a position generally parallel to and aligned with the first longitudinal axis LA1 to a position generally transverse to the first segment 2517. Pivoting of the second segment 2519 is stopped when the inward end 2593 of the second segment 2519 contacts the first stop 2579 of the first segment 2517. Further, as the tip assembly 2505 transitions from the collapsed configuration to the expanded configuration, the third segment 2521 pivots about the second pivot pin 2591 in a radially outward direction from a position generally parallel to and aligned with the first longitudinal axis LA1 to a position generally parallel to and radially outward from the first longitudinal axis LA1. Pivoting of the third segment 2521 is stopped when the distal end 2595 of the third segment 2521 contacts the second stop 2581 of the second segment 2519.

When tension on the pull wire 2571 is released, the biasing of the first and second pivot pins 2589 and 2591 permit the tip assembly 2505 to transition from the expanded configuration of FIG. 28 to the collapsed configuration of FIG. 25.

While the system 2501 of FIGS. 25-29 has been described with a specific configuration, this is by way of example and not limitation. For example, in another embodiment, the tip assembly 2505 may be biased to the expanded configuration. In yet another embodiment, the tip assembly 2505 can be formed from a shape memory material and be restrained and delivered to the desired site in the collapsed configuration wherein once positioned, the restraint may be removed and the tip assembly 2505 permitted to self-expand. "Self-expand" as used herein means that the tip assembly 2505 has a mechanical memory to return to the expanded configuration. The salient factor herein is that the tip assembly 2505 includes the collapsed configuration for delivery and the expanded configuration for ultrasonically fracturing a frame of a deployed valve prosthesis. Accordingly, the tip assembly 2505 may include any configuration suitable to transition the tip assembly 2505 from the collapsed delivery configuration to the expanded configuration.

A system 3001 for fracturing a frame of a deployed valve prosthesis, such as the frame 102 of the valve prosthesis 100 previously described herein, with ultrasonic vibration according to yet another embodiment hereof is shown in FIGS. 30A-32. The system 3001 includes a first shaft 3003, a second shaft 3050, a first tip assembly 3005, a second tip assembly 3052, an ultrasonic electric generator 3007, and an ultrasonic transducer 3009. The first shaft 3003, ultrasonic electric generator 3007, and the ultrasonic transducer 3009 are similar to the shaft 1503, the ultrasonic electric generator 1507, and the ultrasonic transducer 1509 and therefore are not described in detail with respect to FIGS. 30A-32.

Figure 30A:
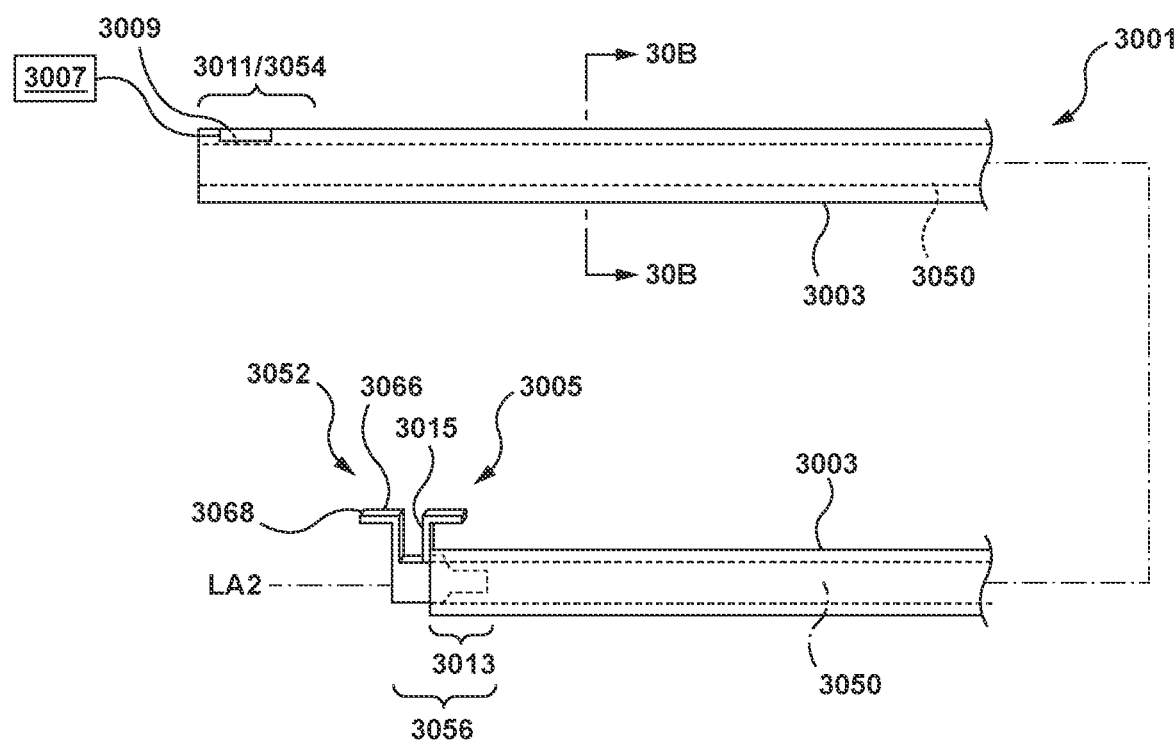
FIG. 30A depicts a side view illustration of a system according to an embodiment hereof, wherein the system includes a first tip assembly and a second tip assembly according to an embodiment hereof.
Figure 30B:
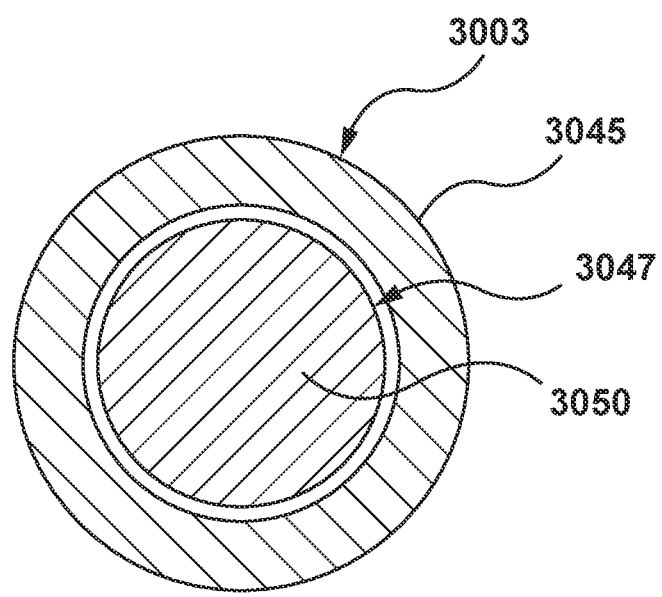
FIG. 30B depicts a cross-sectional illustration of the system taken along the line 30B-30B of FIG. 30A.
Figure 31:
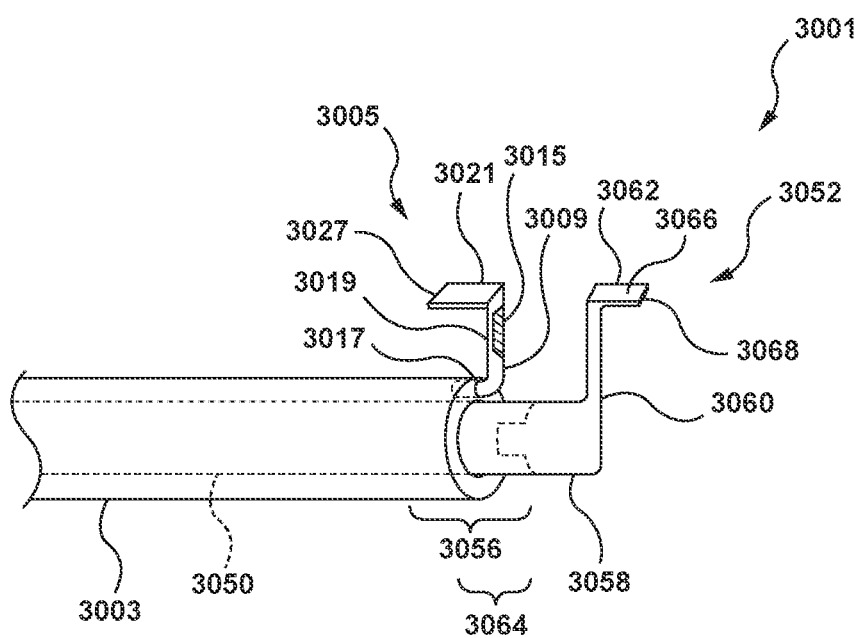
FIG. 31 depicts a close-up perspective illustration of a distal portion of the system of FIG. 30A.

In the embodiment of FIGS. 30A-32, as best shown in FIG. 31, the first tip assembly 3005 includes a sharpened edge 3015, a first segment 3017, a second segment 3019, and a third segment 3021. The first tip assembly 3005 is similar to the tip assembly 1505 of FIGS. 15A-16, except that a third segment 3021 of the first tip assembly 3005 extends proximally from a second segment 3019 of the first tip assembly 3005. Therefore, similar construction and alternatives will not be repeated. It will be understood that in the embodiment of FIGS. 30A-32 the first tip assembly 3005 includes the sharpened edge 3015 disposed on a distal facing surface 3029 of the second segment 3019, which is a close up perspective view of the first and second tip assemblies 3005, 3052, respectively. While the embodiment of FIGS. 30A-32 illustrates the tip assembly 3005 with a flat third segment 3021 and a square tip 3027 similar to the flat third segment 2321 of FIGS. 23 and 24, this is by way of example and not limitation. It will be understood that the third segment 3021 may have other configurations including but not limited to the flat rounded configuration of FIGS. 21 and 22, or any other suitable configuration.

The second shaft 3050 is a flexible catheter shaft with a shaft wall 3045 having a generally tubular shape. The second shaft 3050 is configured to be slidably and rotatably disposed within a lumen 3047 of the first shaft 3003, as best viewed in the cross-section illustration of FIG. 30B. The second shaft 3050 includes a proximal portion 3054 and a distal portion 3056. In the embodiment of FIGS. 30A-32, the second shaft 3050 is configured to translate movement from the proximal portion 3054 to the distal portion 3056. More specifically, the second shaft 3050 is configured to translate movement from the proximal portion 3054 to the second tip assembly 3052 coupled to the distal portion 3056. Although the second shaft 3050 is described herein as a single component, this is by way of example and not limitation, and the second shaft 3050 may include components such as, but not limited to a proximal shaft, a distal shaft, a handle, or other components suitable for the purposes described herein. The second shaft 3050 may be constructed of materials such as, but not limited to stainless steel, titanium, tungsten, tantalum, or other materials suitable for the purposes of the present disclosure.

The second shaft 3050 is configured to be disposed with a portion thereof extending outside of a patient, i.e., the proximal portion 3054, and a portion thereof positioned in situ within a body lumen or vessel, i.e., the distal portion 3056. The second shaft 3050 is further configured to deliver and position the second tip assembly 3052 of the system 3001 at the site of the deployed valve prosthesis 100, as described below. Accordingly, the second shaft 3050 and the second tip assembly 3052 are each sized and configured to be advanced through a vasculature in a minimally invasive manner.

As best viewed in FIG. 31, the second tip assembly 3052 includes a first segment 3058, a second segment 3060, and a third segment 3062. A proximal portion 3064 of the second tip assembly 3052 is coupled to the distal portion 3056 of the second shaft 3050. The second tip assembly 3052 is configured to hold or stabilize a distal portion of the frame 102 of the deployed valve prosthesis 100 as the first tip assembly 3005 fractures the frame 102 of the deployed valve prosthesis 100. In the embodiment of FIGS. 30A-32, the first segment 3058 and the second segment 3060 of the tip assembly 305 each include a generally tubular shape with a generally circular cross-section. The third segment 3062 includes a generally flat or planar shape with a generally rectangular cross-section. The second tip assembly 3052 may be constructed of materials such as, but not limited to stainless steel, nickel-titanium alloys (i.e. NITINOL), or other materials suitable for the purposes of the present disclosure. The second tip assembly 3052 may be coupled to the second shaft 3050, by methods such as, but not limited to adhesives, welding, clamping, or other coupling methods as appropriate. While the second tip assembly 3052 is shown coupled to the second shaft 3050 in a particular coupling configuration, this is by way of example and not limitation, and it will be understood that other coupling configurations may be utilized. For example, and not by way of limitation, a proximal end of the second tip assembly 3052 may be coupled to a distal end of the second shaft 3050. Further, while the first and second segments 3058 and 3060 of the tip assembly 305 have each been described with a generally tubular shape and a generally circular cross-section, this is by way of example and not limitation. The first and second segments 3058 and 3060 may each have alternative shapes including, but not limited to shapes with an oblong cross-section, a rectangular cross-section, or any other suitable shape. Even, further, while the third segment 3062 has been described with a generally flat, rectangular shape with a generally rectangular cross-section, this is again by way of example and not limitation. The third segment 3062 may have alternative shapes including, but not limited to rounded, oblong, or conical shapes and a circular or oblong cross-section, or any other suitable shape.

Figure 32:
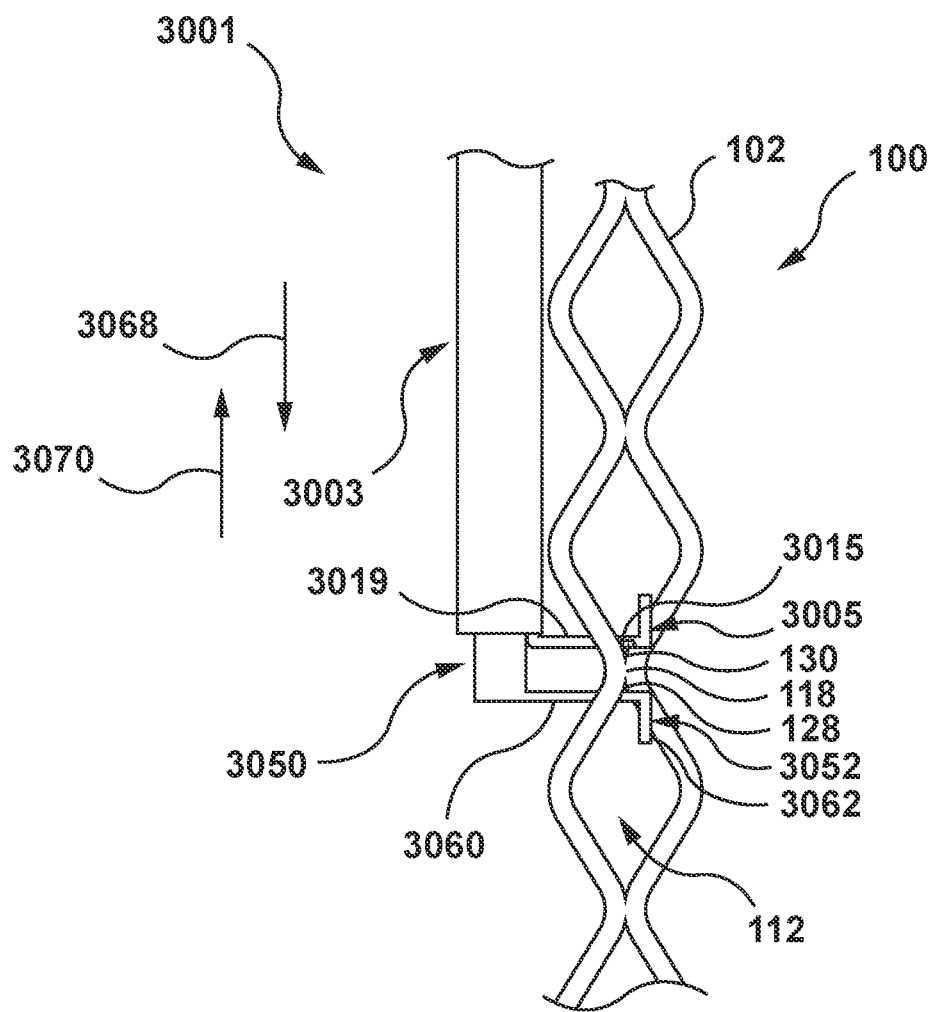
FIG. 32 depicts a close-up perspective illustration of the tip assembly of the system of FIG. 30A, wherein each tip assembly is adjacent to and in contact with the desired connection point of the frame of the deployed valve prosthesis.

The first segment 3058 includes a second longitudinal axis LA2, as best shown in FIG. 30A. The second segment 3060 of the second tip assembly 3052 extends radially outward from, or generally transverse to the first segment 3058. The third segment 3062 extends distally from the second segment 3060 such that the third segment 3062 is generally parallel to and radially outward from the second longitudinal axis LA2. In the embodiment of FIGS. 30A-32, the third segment 3062 includes a flat portion 3066 and a square tip 3068 at a distal portion thereof. The third segment 3062 is configured such that the third segment 3062 will not damage tissue during delivery of the second tip assembly 3052 to the deployed valve prosthesis 100 or during fracturing of the frame 102. While the second tip assembly 3052, and more precisely the first segment 3058, the second segment 3060, and the third segment 3062 have been described herein as a single component, this is not meant to limit the design and the first segment 3058, the second segment 3060, and the third segment 3062 may be separate components coupled together by methods such as but not limited adhesives, welding, or other coupling methods as appropriate The interaction of the various components of the system 3001 will now be described to fracture a connection point, such as the connection point 118 of the frame 102 of the deployed valve prosthesis 100 with reference to FIG. 32. With the components of the system 3001 assembled and configured as described above, the system 3001 is advanced to the site of the deployed valve prosthesis 100. The first tip assembly 3005 is manipulated to place the sharpened edge 3015 in contact with an inflow facing surface 130 of the connection point 118 to be fractured, as shown in FIG. 32 and as previously described with respect to the first tip assembly 305 of FIGS. 4 and 5A-5C.

The third segment 3062 of the tip assembly 3052 is brought into apposition with the desired connection point 118 to be fractured. The second tip assembly 3052 is manipulated to position the second segment 3060 in contact with the connection point 118 to be fractured on the opposite side of the connection point 118 to the first tip assembly 3005. In the embodiment of FIG. 32, this includes manipulating the second tip assembly 3052 radially outward such that the third segment 3062 passes through one cell 112 of the frame 102 that is adjacent to an outflow facing surface 128 of the desired connection point 118 to be fractured.

When the second segments 3019, 3060 of the first and second tip assemblies, 3005, 3052, respectively, are each positioned on opposite sides of the connection with the desired connection point 118 sandwiched there between, the first shaft 3003 is distally advanced to place the sharpened edge 3015 in contact with the inflow facing surface 130 of the connection point 118 to be fractured, and the second shaft 3050 is proximally retracted to place the second shaft 3019 in contact with the outflow facing surface 128 of the connection point 118 to be fractured, as best shown in FIG. 32. It will be understood that only a portion of the frame 102 is illustrated in FIG. 32, and that the omitted portions of the frame 102 have been omitted for clarity.

A first constant force in the distal direction, indicated in FIG. 32 by an arrow 3068, is maintained on the first shaft 3003 to keep the sharpened edge 3015 in contact with the desired connection point 118 and a second constant force in the proximal direction, indicated in FIG. 32 by an arrow 3070, is meant maintained on the second shaft 3050 to keep the second segment 3019 in contact with the desired connection point 118.

When the first constant force in the distal direction (indicated by the arrow 3068) is holding the sharpened edge 3015 in contact with the desired connection point 118 and the second constant force in the proximal direction (indicated by the arrow 3070) is holding the second segment 3019 in contact with the desired connection point 118, the ultrasonic electric generator 3007 and the ultrasonic transducer 3009 are activated. The ultrasonic vibration of the ultrasonic transducer 3009 is translated to a coupled proximal portion 3011 (shown in FIG. 30A) of the first shaft 3003. The shaft 3003 translates the ultrasonic vibration to a distal portion 3013 of the first shaft 3003, and to the first tip assembly 3005 coupled thereto. The sharpened edge 3015 of the first tip assembly 3005 focuses the mechanical vibration onto the contacted desired connection point 118. The second constant force in the proximal direction (indicated by the arrow 3070) holds the second segment 3019 of the second shaft 3050 in contact with the desired connection point 118 to stabilize the connection point 118 during fracturing. Stabilizing of the connection point 118 during ultrasonic fracturing provides additional force to keep the sharpened edge 3015 of the first tip assembly 3005 in contact with the connection point 118, thereby preventing the system 3001 from moving relative to the frame 102 and damaging the surrounding tissue during fracturing.

When the desired connection point 118 has been fractured, the ultrasonic electric generator 3007 and the ultrasonic transducer 3009 are deactivated. If another connection point 118 is to be fractured, the process of maneuvering the first and the second tip assemblies 3005 and 3052, respectively, to the next desired connection point 118 and fracturing of said next desired connection point 118 is repeated.

While described herein with the sharpened edge 3015 disposed on the first tip assembly 3005, this is by way of example and not limitation. For example, in another embodiment hereof, the sharpened edge 3015 is disposed on a distal facing surface of the second segment 3060 of the second tip assembly 3052 and the second shaft 3050 is configured to translate ultrasonic vibrations from the ultrasonic electric generator 3007 and the ultrasonic transducer 3009 to the second tip assembly 3052. In yet another embodiment hereof, the second segment 3019 of the first tip assembly 3005 and the second segment 3060 of the second tip assembly 3052 each include a sharpened edge 3015, and both the first shaft 3003 and the second shaft 3050 are each configured to translate ultrasonic vibrations to the respective first and second tip assemblies 3005, 3052 to fracture the desired connection point 118.

As described above, by focusing the ultrasonic vibration onto a known point, i.e. the desired connection point, tip assemblies according to embodiments hereof break or fracture a frame of a deployed prosthesis at a known location and in a known and predictable manner that provides a level of embolic protection by reducing or eliminating the creation of shards during the fracturing process. However, in addition, embolic protection devices may be utilized with any embodiment hereof. More particularly, embolic protection devices are known to one of ordinary skill in the art to deal with debris or fragments that are dislodged in the circulatory system during treatment procedures. One protection technique includes the temporary placement of an intravascular filter or trap downstream from the treatment site to capture debris before it can reach and embolize smaller blood vessels downstream. The placement of a filter in the patient's vasculature during treatment can collect embolic debris in the bloodstream. At the end of the treatment procedure, the filter can be removed along with the captured debris. Such filters typically comprise a filtration membrane, mesh or "basket" having a plurality of pores, each pore being sized to prevent passage of particulate larger than a certain size, e.g., 100-200 microns. Conventionally, embolic filters are positioned downstream from the treatment device such that the filter may be deployed in a location that does not interfere or interact with the treatment device. For example, it is known to attach an expandable filter to a guidewire or guidewire-like member that allows the filtering device to be placed in the patient's vasculature. The guidewire allows the physician to steer the filter to a location downstream from the area of treatment. Once the guidewire is in proper position in the vasculature, the embolic filter can be deployed to capture embolic debris. Treatment devices then can be delivered to the area of treatment by tracking over the guidewire or guidewire-like member.

In addition, image guidance, enhanced echogenicity, or other methods may be used to aid the clinician's delivery and positioning of any system described herein. Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's positioning and manipulation of the systems described herein at the target site of a deployed valve prosthesis. For example, such image guidance technologies can be used to aid in determining the positioning of the tip assemblies described herein with relation to the deployed valve prosthesis and the target region thereof that is to be fractured by the tip assembly. In some embodiments, image guidance components (e.g., IVUS, OCT) can be coupled to the distal portion of the shaft, the tip assembly, or both to provide three-dimensional images of the area proximate to the target deployed valve prosthesis to facilitate positioning, orienting and/or deployment of the systems described herein within the target site of a deployed valve prosthesis. Accordingly, an echogenic coating may be applied to components of the system to aid in visualization.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

What is claimed is:

1. A method of fracturing a frame of a deployed prosthesis, the method comprising:
   advancing a system to a site of the deployed prosthesis, wherein the system includes a shaft, a tip assembly, an ultrasonic electric generator, and an ultrasonic transducer;
   positioning the tip assembly of the system in apposition with a portion of the frame of the deployed prosthesis;
   placing a cutting edge of the tip assembly in contact with the portion of the frame;
   applying a first longitudinal force to the shaft such that the cutting edge maintains contact with the portion of the frame; and
   activating the ultrasonic generator and the ultrasonic transducer to vibrate the tip assembly to fracture the portion of the frame.

2. The method of claim 1, wherein the method steps are repeated for each portion of the frame to be fractured.

3. The method of claim 1, wherein the cutting edge of the tip assembly is placed in contact with a proximal facing surface of the portion of the frame to be fractured and the shaft is distally advanced to apply the first longitudinal force to maintain contact between the cutting edge and the portion of the frame.

4. The method of claim 1, wherein the cutting edge of the tip assembly is placed in contact with a distal facing surface of the portion of the frame to be fractured and the shaft is proximally retracted to apply the first longitudinal force to maintain contact between the cutting edge and the portion of the frame.

5. The method of claim 1, wherein the deployed prosthesis is an aortic valve prosthesis deployed at a native aortic valve.

6. The method of claim 1, wherein the frame comprises struts, crowns, and connection points, and wherein the portion of the frame to be fractured is a first connection point.

7. The method of claim 6, wherein the first connection point connects longitudinally adjacent crowns of the frame.

8. The method of claim 7, further comprising:
   moving the tip assembly of the system in apposition with a second connection point of the frame of the deployed prosthesis;
   placing the cutting edge of the tip assembly in contact with the second connection point of the frame;
   applying a second longitudinal force to the shaft such that the cutting edge maintains contact with the second connection point of the frame; and
   activating the ultrasonic generator and the ultrasonic transducer to fracture the second connection point of the frame.

9. The method of claim 8, wherein the second connection point is longitudinally aligned with the first connection point.

10. The method of claim 7, further comprising:
moving the tip assembly of the system in apposition with a third connection point of the frame of the deployed prosthesis;
placing the cutting edge of the tip assembly in contact with the third connection point of the frame;
applying a third longitudinal force to the shaft such that the cutting edge maintains contact with the third connection point of the frame; and
activating the ultrasonic generator and the ultrasonic transducer to fracture the third connection point of the frame.

11. The method of claim 10, wherein the first, second, and third connections points are longitudinally aligned.

12. The method of claim 1, further comprising:
moving the tip assembly of the system in apposition with a second portion of the frame of the deployed prosthesis;
placing the cutting edge of the tip assembly in contact with the second portion of the frame;
applying a second longitudinal force to the shaft such that the cutting edge maintains contact with the second portion of the frame; and
activating the ultrasonic generator and the ultrasonic transducer to fracture the second portion of the frame.

13. The method of claim 12 further comprising:
moving the tip assembly of the system in apposition with a third portion of the frame of the deployed prosthesis;
placing the cutting edge of the tip assembly in contact with the third portion of the frame;
applying a third longitudinal force to the shaft such that the cutting edge maintains contact with the third connection portion of the frame; and
activating the ultrasonic generator and the ultrasonic transducer to fracture the third portion of the frame.

14. The method of claim 1, wherein positioning the tip assembly of the system in apposition with a portion of the frame of the deployed prosthesis further comprises positioning a segment of the tip assembly between an outer surface of the frame and tissue at the site of the deployed prosthesis.

15. The method of claim 1, wherein the deployed prosthesis is a valve prosthesis and the site of the deployed prosthesis is a native heart valve.

16. The method of claim 1, wherein the deployed prosthesis is an aortic valve prosthesis and the site of the deployed prosthesis is a native aortic valve.

* * * * *